US011065439B1

(12) United States Patent
Halpern

(10) Patent No.: US 11,065,439 B1
(45) Date of Patent: Jul. 20, 2021

(54) CONFORMING MODULAR NEURAL INTERFACE SYSTEM

(71) Applicant: Modular Bionics Inc., Berkeley, CA (US)

(72) Inventor: Ian Loren Halpern, Mill Valley, CA (US)

(73) Assignee: Modular Bionics Inc., Berkeley, CA (US)

( * ) Notice: Subject to any disclaimer, the term of this patent is extended or adjusted under 35 U.S.C. 154(b) by 159 days.

(21) Appl. No.: 16/216,797

(22) Filed: Dec. 11, 2018

Related U.S. Application Data

(60) Provisional application No. 62/597,316, filed on Dec. 11, 2017.

(51) Int. Cl.
*A61N 1/05* (2006.01)
*A61N 1/36* (2006.01)
*A61B 5/00* (2006.01)
*A61B 5/24* (2021.01)

(52) U.S. Cl.
CPC ............. *A61N 1/0504* (2013.01); *A61B 5/24* (2021.01); *A61B 5/686* (2013.01); *A61N 1/36082* (2013.01); *A61N 1/36128* (2013.01)

(58) Field of Classification Search
USPC ......................................................... 607/118
See application file for complete search history.

(56) References Cited

U.S. PATENT DOCUMENTS

| | | | |
|---|---|---|---|
| 4,151,365 A | 2/1979 | Fischell et al. | |
| 4,154,228 A | 5/1979 | Feldstein et al. | |
| 4,207,903 A | 6/1980 | O'Neill | |
| 4,213,465 A | 7/1980 | Renheim | |
| 4,441,498 A | 4/1984 | Nordling | |
| 4,461,304 A | 7/1984 | Kuperstein | |
| 4,573,481 A | 3/1986 | Bullara | |
| 4,640,983 A | 2/1987 | Comte | |
| 4,920,979 A | 5/1990 | Bullara | |
| 4,964,414 A | 10/1990 | Handa et al. | |
| 5,215,088 A | 6/1993 | Normann et al. | |
| 5,361,760 A | 11/1994 | Normann et al. | |
| 5,645,586 A | 7/1997 | Meltzer | |

(Continued)

FOREIGN PATENT DOCUMENTS

| EP | 1985579 | 10/2008 |
|---|---|---|
| WO | WO 2010/138228 | 12/2010 |
| WO | WO 2013/096873 | 6/2013 |

OTHER PUBLICATIONS

U.S. Appl. No. 15/192,905, filed Jun. 24, 2016, Halpern et al.

(Continued)

*Primary Examiner* — Nicole F Lavert
*Assistant Examiner* — Nichole F Johnson
(74) *Attorney, Agent, or Firm* — Knobbe, Martens, Olson & Bear, LLP

(57) ABSTRACT

Disclosed herein are systems, devices, and methods for better conforming to biological tissue, reducing the temperature and irritation of tissue, modulating tissue, and/or wirelessly sending and receiving power through tissue. Devices can include panels movable with respect to each other to allow the body to move between a flattened and non-flattened state. Devices can include movable parts or structures that enable improved conformance to three-dimensional surfaces of tissue.

20 Claims, 15 Drawing Sheets

(56) References Cited

U.S. PATENT DOCUMENTS

| | | | |
|---|---|---|---|
| 5,938,689 A | 8/1999 | Fischell et al. |
| 6,002,957 A | 12/1999 | Finneran |
| 6,009,350 A | 12/1999 | Renken |
| 6,135,968 A | 10/2000 | Brounstein |
| 6,215,454 B1 | 4/2001 | Tran |
| 6,304,785 B1 | 10/2001 | McCreery et al. |
| 6,447,530 B1 | 9/2002 | Ostrovsky et al. |
| 6,456,256 B1 | 9/2002 | Amundson et al. |
| 6,560,479 B2 | 5/2003 | van Drongelen |
| 6,705,900 B2 | 3/2004 | Sommer et al. |
| 6,719,582 B1 | 4/2004 | Swanson |
| 6,748,260 B2 | 6/2004 | Au et al. |
| 6,829,498 B2 | 12/2004 | Kipke et al. |
| 6,921,295 B2 | 7/2005 | Sommer et al. |
| 6,924,773 B1 | 8/2005 | Paratte |
| 6,965,794 B2 | 11/2005 | Brody |
| 7,006,859 B1 | 2/2006 | Osorio et al. |
| 7,010,356 B2 | 3/2006 | Jog et al. |
| 7,149,578 B2 | 12/2006 | Edvardsson |
| 7,162,310 B2 | 1/2007 | Doan |
| 7,203,548 B2 | 4/2007 | Whitehurst et al. |
| 7,212,851 B2 | 5/2007 | Donoghue et al. |
| 7,299,089 B2 | 11/2007 | Wolf et al. |
| 7,343,205 B1 | 3/2008 | Pianca et al. |
| 7,460,904 B2 | 12/2008 | Deadwyler et al. |
| 7,548,775 B2 | 6/2009 | Kipke et al. |
| 7,551,951 B1 | 6/2009 | Osorio et al. |
| 7,729,758 B2 | 6/2010 | Haller et al. |
| 7,751,877 B2 | 7/2010 | Flaherty et al. |
| 7,805,175 B2 | 9/2010 | Lin et al. |
| 7,991,475 B1 | 8/2011 | Tang et al. |
| 8,024,022 B2 | 9/2011 | Schulman et al. |
| 8,027,735 B1 | 9/2011 | Tzivskos et al. |
| 8,086,322 B2 | 12/2011 | Schouenborg |
| 8,090,448 B2 | 1/2012 | Greenberg et al. |
| 8,112,160 B2 | 2/2012 | Foster |
| 8,160,696 B2 | 4/2012 | Bendett et al. |
| 8,224,459 B1 | 7/2012 | Pianca et al. |
| 8,255,061 B2 | 8/2012 | Perlin et al. |
| 8,498,694 B2 | 7/2013 | McGuire, Jr. et al. |
| 8,774,937 B2 | 7/2014 | Mercanzini et al. |
| 8,958,868 B2 | 2/2015 | Ghovanloo et al. |
| 9,095,267 B2 | 8/2015 | Halpern et al. |
| 9,240,630 B2 | 1/2016 | Joshi |
| 10,086,192 B2 | 10/2018 | Halpern et al. |
| 10,368,761 B2 | 8/2019 | Halpern et al. |
| 10,674,914 B1 | 6/2020 | Halpern et al. |
| 10,874,847 B2 | 12/2020 | Halpern et al. |
| 2004/0082875 A1 | 4/2004 | Donoghue et al. |
| 2004/0199235 A1 | 10/2004 | Younis |
| 2005/0021117 A1 | 1/2005 | He et al. |
| 2006/0173263 A1 | 8/2006 | He et al. |
| 2006/0178655 A1 | 8/2006 | Santini, Jr. et al. |
| 2006/0276882 A1 | 12/2006 | Case et al. |
| 2007/0191906 A1 | 8/2007 | Iyer et al. |
| 2008/0044449 A1 | 2/2008 | McKay |
| 2008/0177364 A1 | 7/2008 | Bolea et al. |
| 2008/0249443 A1 | 10/2008 | Avitable et al. |
| 2009/0099441 A1 | 4/2009 | Giszter et al. |
| 2009/0112278 A1 | 4/2009 | Wingeier et al. |
| 2009/0157141 A1 | 6/2009 | Chiao et al. |
| 2009/0177144 A1 | 7/2009 | Masmanidis et al. |
| 2010/0023021 A1 | 1/2010 | Flaherty |
| 2010/0178810 A2 | 7/2010 | Aarts et al. |
| 2010/0198281 A1 | 8/2010 | Chang et al. |
| 2010/0292759 A1 | 11/2010 | Hahn et al. |
| 2011/0144467 A1 | 6/2011 | Yao et al. |
| 2011/0144639 A1 | 6/2011 | Govari |
| 2011/0288619 A1 | 11/2011 | Pianca |
| 2012/0083719 A1 | 4/2012 | Mishelevich |
| 2012/0123289 A1 | 5/2012 | Sorenson et al. |
| 2012/0203129 A1 | 8/2012 | Rennaker |
| 2012/0277834 A1* | 11/2012 | Mercanzini ........ A61N 1/36082 607/62 |
| 2012/0302856 A1 | 11/2012 | Chang et al. |
| 2013/0002519 A1 | 1/2013 | Camacho et al. |
| 2013/0172717 A1 | 7/2013 | Halpern et al. |
| 2014/0094674 A1 | 4/2014 | Nurmikko et al. |
| 2014/0213891 A1 | 7/2014 | Gilgunn et al. |
| 2015/0335883 A1 | 11/2015 | Halpern et al. |
| 2015/0360030 A1* | 12/2015 | Cartledge ............ A61N 1/0472 607/60 |
| 2018/0008819 A1 | 1/2018 | Halpern et al. |
| 2019/0240478 A1 | 8/2019 | Halpern et al. |
| 2020/0163565 A1 | 5/2020 | Halpern et al. |

OTHER PUBLICATIONS

U.S. Appl. No. 16/148,226, filed Oct. 1, 2018, Halpern et al.
Barna, James S., et al., "A New Multielectrode Array for the Simultaneous Recording of Field Potentials and Unit Activity", Electroencephalography and Clinical Neurophysiology 1981, 52: pp. 494-496.
International Search Report dated Apr. 4, 2013 for PCT App. No. PCT/US2012/071429 in 8 pages.
Jellema et al. "A slim needle-shaped multiwire microelectrode for intracerebral recording." J. Neurosci. Methods, 40 (1991) 203-209.
Karmos, George, et al., "A New Multielectrode for Chronic Recording of Intracortical Field Potentials in Cats", Physiology & Behavior, 1982, vol. 29, pp. 567-570.
Nicolelis, Miguel A.L., "Methods for Neural Ensemble Recordings", CRC Press LLC, 1999, pp. 5-12 in 10 pages.
Plexon Neurotechnology Research Systems, V-Probe Technical Guide 8, 16, 24 and 32 Channels (2013) in 14 pages.
Ulbert, Dr. Istvan, "Investigation of the evoked and spontaneous intracortical electrical activity with multielectrodes in humans", Semmelweis University Doctoral School, Neurosciences, Budapest, 2001, in 101 pages.
Ulbert, Istvan, "Multiple channel microelectrode system for human epilepsy research", IEEE, 2006, pp. 222-225.
Ulbert, Istvan, et al., "In vivo laminar electrophysiology co-registered with histology in the hippocampus of patients with temporal lobe epilepsy", Experimental Neurology, 187 (2004), pp. 310-318.
Ulbert, Istvan, et al., "Multiple microelectrode-recording system for human intracortical applications", Journal of Neuroscience Methods, 106 (2001) 69-79.
U.S. Appl. No. 16/892,626, filed Jun. 4, 2020, Halpern et al.
U.S. Appl. No. 17/101,718, filed Nov. 23, 2020, Halpern et al.

* cited by examiner

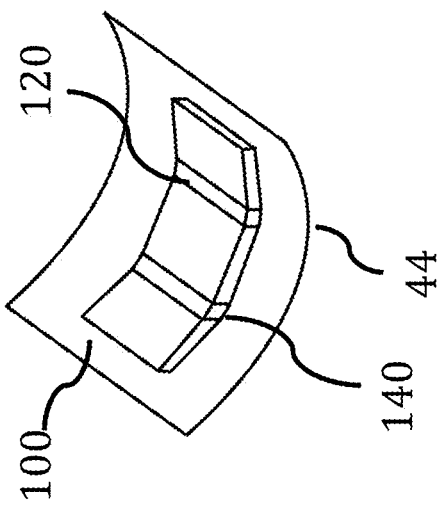
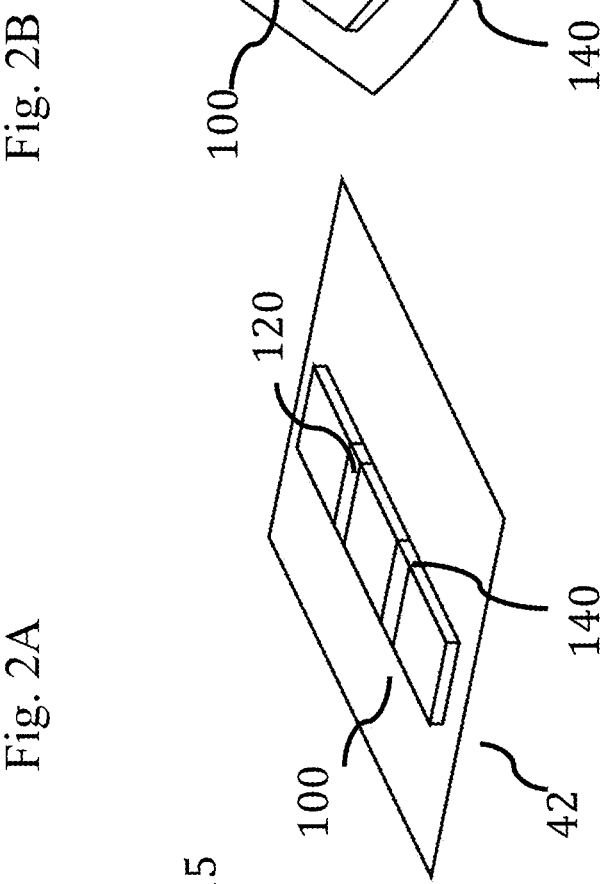
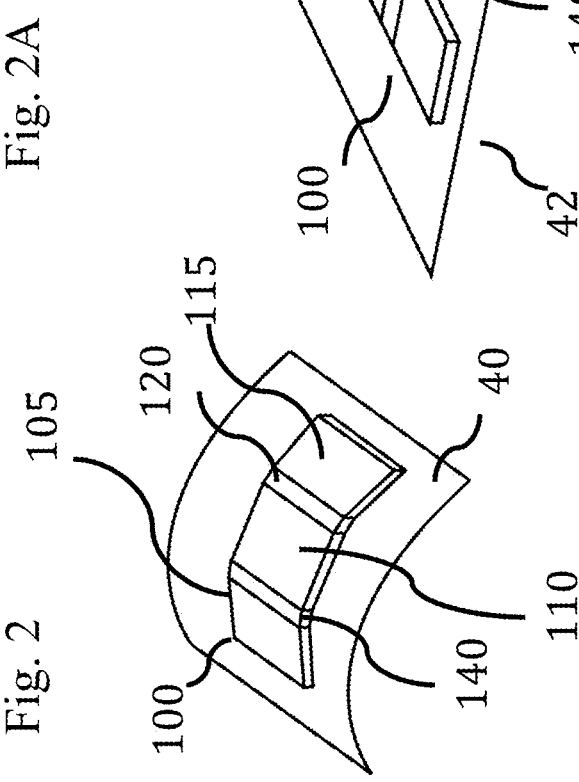

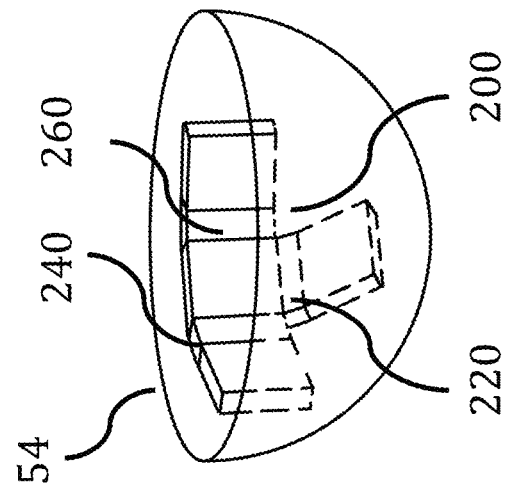
Fig. 3B
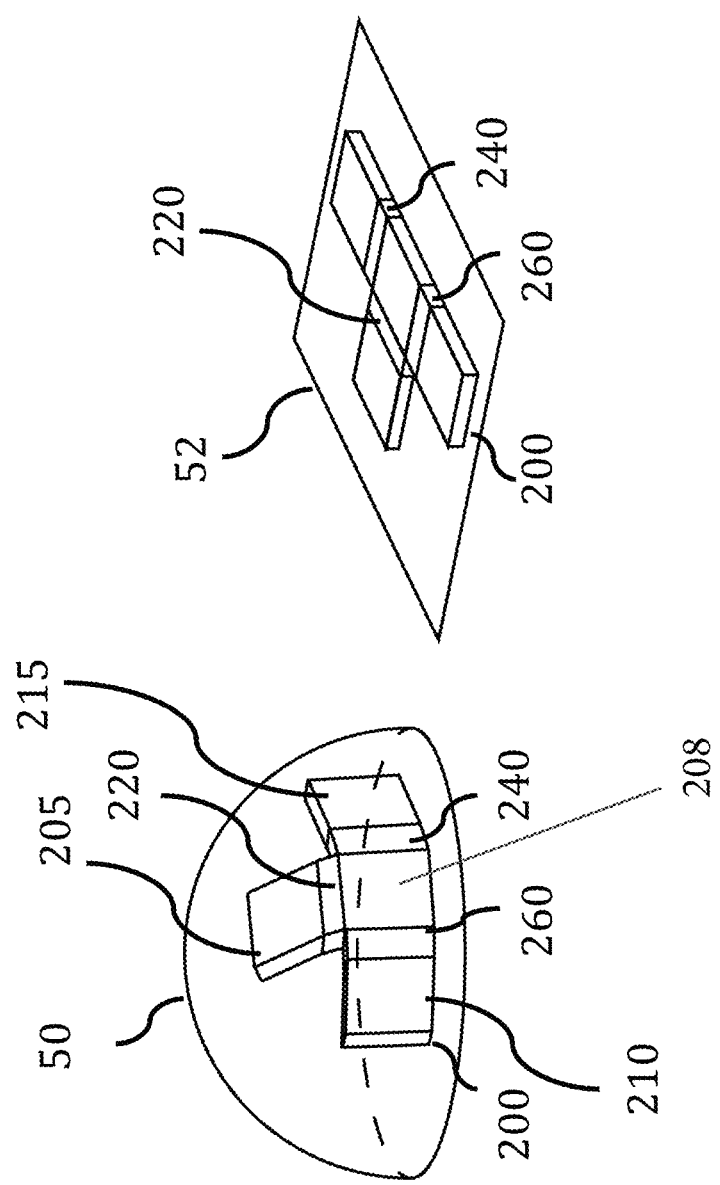
Fig. 3A
Fig. 3

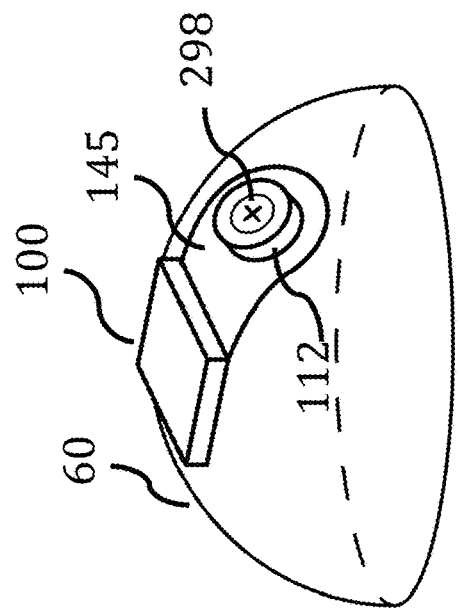
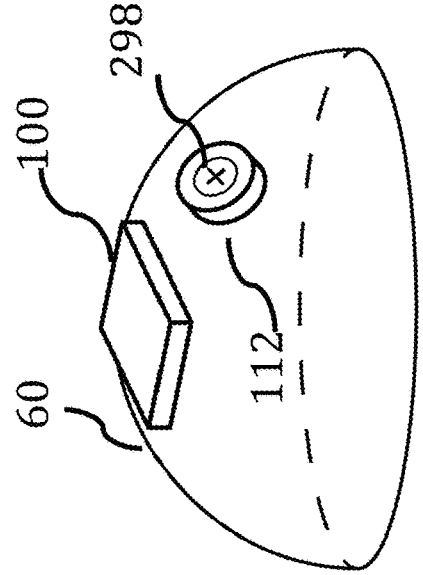
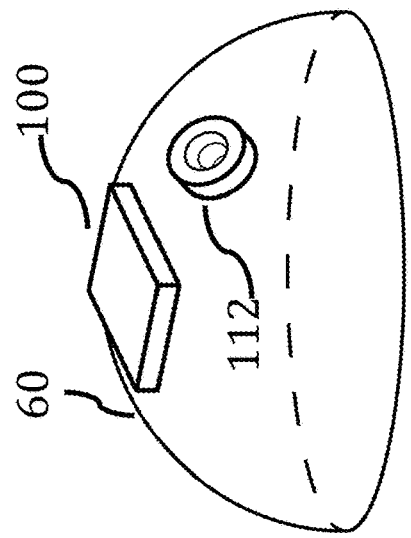

CONFORMING MODULAR NEURAL INTERFACE SYSTEM

REFERENCE TO RELATED APPLICATIONS

This application claims the benefit under 35 U.S.C. § 119(e) as a nonprovisional application of U.S. Pat. App. No. 62/597,316 filed on Dec. 11, 2017, which is incorporated by reference in its entirety. This application also incorporates by reference in its entirety U.S. application Ser. No. 15/192,905 filed on Jun. 24, 2016 and U.S. Prov. App. No. 62/183,867 filed on Jun. 24, 2015.

STATEMENT REGARDING FEDERALLY SPONSORED R&D

This invention was made with government support under contract Number W911NF-16-C-0091 awarded by the United States Army. The government has certain rights in the invention.

BACKGROUND

Some aspects of the present invention relates generally to devices that conform to and interface with the nervous system and other forms of biological tissue. More particularly, some embodiments of the invention relates to devices and systems that can be implanted within tissue or assembled to the external surfaces of tissue to monitor or stimulate the nervous system upon the desired research or clinical purpose.

SUMMARY

Disclosed herein are systems, devices, and methods for better conforming to biological tissue, reducing the temperature and irritation of tissue, modulating tissue, and/or wirelessly sending and receiving power through tissue. Devices can include in some embodiments panels movable with respect to each other to allow the body to move between a flattened and non-flattened state. Devices can include in some embodiments movable parts or structures that enable improved conformance to three-dimensional surfaces of tissue, and over a wide range of tissue, organ, and other biological and non-biological substrate geometries. The movable structures can include hinges in some cases. In some embodiments a device could include, or not include any panels with electrode shanks. In other embodiments, the devices are configured to conform to adjacent tissue and minimize the irritation of tissue, the generation of heat, and the restriction of movement of tissue. In some embodiments, one or more devices are configured at a target substrate. In other embodiments, two or more devices are configured adjacent separate target substrates. In some embodiments, devices are positioned to align the panels of each device. In some embodiments, the devices are positioned without the alignment of their panels. In some embodiments, aligned devices have the same number of panels. In other embodiments, aligned devices have different numbers of panels. In some embodiments, the devices have approximately matching panels. In some embodiments, the devices do not have matching panels. In some embodiments, devices are positioned to align the movable parts or structures of each device. In some embodiments, devices are positioned without the alignment of the movable parts or structures. In some embodiments, aligned devices have the same number of movable parts or structures. In other embodiments, aligned devices have different numbers of movable parts or structures. In some embodiments, the devices have approximately matching movable parts or structures. In some embodiments, the devices do not have matching movable parts or structures. Panels could be made of biocompatible materials, including but not limited to polymer, silicone, titanium, stainless steel, platinum, ceramic, sapphire crystal, glass, gold, silver, and the like. System electronics included on the panels could be made of different materials in some embodiments.

In still other embodiments, two or more devices are configured relative to one another to communicate through wires. In still other embodiments, the devices are configured to wirelessly transfer power and data. The devices can include, for example, a wireless antenna and an inductive coil for the wireless transfer of power. In still other examples, the devices can include heat sinks, fans, and other means of cooling or reducing a rise in temperature. In some embodiments, the devices have a method for assembly and removal from tissue that involves an assembly device that disengages and engages areas of the device that hold it in position such as, for example, magnetic materials.

In some embodiments, the devices and systems are capable of transmitting wireless signals through tissue. The systems can include in some embodiments housings that are transparent to electromagnetic radiation. The systems can also include shielding adjacent antennas. The systems can also include a locating element that aligns an external device with an implanted device. Also, the systems can include housings that are partially transparent to electromagnetic radiation. In some embodiments, an antenna array includes two or more antennas. In still other embodiments, a device is operably connected to a neural probe. In some embodiments, a worn device can relay information wirelessly to another device. In other embodiments, the wirelessly transmitted information can include neural signals, heart rhythms, muscle firing signals, images, and video. In some embodiments, also disclosed herein is a neural interface. The neural interface can include a housing configured to be implanted at a location in a patient under a skull and proximate neural tissue; a first antenna within the housing and configured to transmit neural data wirelessly to an external device; and a second antenna within the housing and configured to transmit neural data wirelessly to an external device. In some embodiments, the first antenna and the second antenna transmit the neural data on the same or an overlapping frequency spectrum. The housing can include shielding partially surrounding the first antenna and second antenna. The housing can also include one, two, or more shielding-free windows that allow the first antenna and the second antenna to allow wireless transmission at angles between about 90 degrees and about 180 degrees with respect to a long axis of the window. In some embodiments, the neural interface can also include a third antenna. The third antenna can be unshielded. In some embodiments, the third antenna transmits data on a frequency spectrum different from (not overlapping with) that of the first antenna and the second antenna. In some embodiments, the first antenna and the second antenna are spaced apart and separated by a wall. In some embodiments with three or more antennas, each antenna can be spaced apart by one or more walls. The wall can be dynamically movable. The shielding can extend laterally in one or more directions beyond the first antenna and the second antenna. The shielding can extend laterally by a distance of between about 0.1 mm and about 10 mm. There can be an air gap between the one or more windows and the antennas. The first antenna and the second antenna can transmit the neural data via an ultrawideband protocol. The neural interface can also include a third antenna and a fourth antenna forming a pair of antennas. The first antenna and the second antenna can be configured to record data, and the third and fourth antennas are configured to send or receive stimulation commands. The first, second, third, and fourth antennas can be part of a closed-loop control system. The neural interface can also include a first antenna array and a second antenna array. The housing can also include a processor configured to compare the frequency and/or modulation of a signal of communication of the first antenna array and the second antenna array. In some embodiments, the first antenna and the second antenna are oriented such that the first antenna can include a first dead zone comprising a first non-transmissible or attenuated volume within the housing and the second antenna includes a second dead zone comprising a second non-transmissible or attenuated volume within the housing. The first volume and the second volume can overlap by at least about 10%, 20%, 30%, 40%, 50%, 60%, 70%, 80%, 90%, or more. In some embodiments, each antenna or pair of antennas could be enclosed in its own discrete housing. In some embodiments, the systems can contain light emitters and light detectors.

In some embodiments, the devices are powered through wires. In still other embodiments, devices are powered through inductive coils. The devices can transmit power to other devices through tissue.

In some embodiments, the devices communicate with one another through wires. In still other embodiments, the devices wirelessly communicate with one another. The devices can wirelessly communicate with one another through the skin and/or other tissues.

In some embodiments, the system utilizes magnetic force to position individual devices. Individual devices can include magnetic materials that attract them to other components containing magnetic materials. Individual devices can apply a magnetic force to one another to maintain an advantageous alignment. An advantageous alignment can include positioning for inductive power transmission and wireless data transmission. An advantageous alignment can also include maintaining the conformance with tissue, and displacing with tissue as it moves. An advantageous alignment can also reduce the increase in temperature of a device. An advantageous alignment can also prevent a device from displacing during use.

In some embodiments, the systems or individual devices can be positioned in a single location within tissue or distributed throughout multiple locations within tissue. In some embodiments, a device is not adjacent tissue, e.g., does not directly contact tissue. In some embodiments, the device is internal to the body, e.g., under the skin surface. In still other embodiments, a device is assembled external to clothing worn on the body, or external to the body and directly on the skin surface.

In some embodiments, a device can have a single movable part or structure, enabling it to displace. The displacement can allow the device to conform to tissue. A device can also include no less than two and no more than twenty, or more than twenty movable parts or structures, enabling it to displace. In some embodiments, one or more devices can be configured to have a first substantially flat or planar configuration and a second substantially non-flat or planar configuration with a radius of curvature of between about 5 mm and about 500 mm, such as about 30 mm, 50 mm, 70 mm, 100 mm, 150 mm, 200 mm, 250 mm, or ranges including any two of the aforementioned values to advantageously conform to a wide range of substrate surface geometries.

In some embodiments, a systems or an individual device can contain one, two, or more movable parts or structures aligned orthogonal to other movable parts or structures.

In some embodiments, a device can have two or more movable parts or structures orthogonal to two or more other movable parts or structures.

In some embodiments, a device can be positioned adjacent a first target substrate of tissue, and another device can be positioned adjacent a second target substrate. In some embodiments, a device can be positioned adjacent a target substrate of tissue, and another device can be positioned adjacent a separate target substrate of tissue. In some embodiments, the systems can include one, two, or more devices implanted within tissue.

In other embodiments, the systems can have one or more devices assembled to the outer surface of the body. In some embodiments, the systems can have one or more devices implanted within tissue, and one or more devices assembled to the outer surface of the body. In some embodiments, the systems can have devices assembled adjacent a single target substrate of tissue.

In some embodiments, devices can be positioned by magnetic force. In some embodiments, devices can be partially held in position by adjacent tissue. In some embodiments, devices can be partially held in position by osseointegration or tissue ingrowth. In some embodiments, devices can be partially held in position by screws. In some embodiments, devices can be partially held in position by sutures, clips, adhesives, magnets, or other permanent or reversible fixation elements.

In some embodiments, the systems or individual devices can be configured to have a geometry and mechanisms capable of accelerating the dissipation of heat.

In some embodiments, protrusions, external guards, or stop surfaces are used to protect against excessive displacement of panels. In some embodiments, protrusions or external guards are used to protect against excessive displacement of movable parts or structures. The protrusions or external guards can prevent devices from dislodging from tissue, collapsing, or hyper-extending in a non-useful displacement. In some embodiments, the polarity of magnets can also be set so that different sections repel one another to prevent potentially damaging over-rotation or hyperextension of sections of the system. In some embodiments, a device can have a power on/off switch that is mechanical, magnetic, infrared or wireless. The polarity of magnets can also be set so that different sections repel one another to prevent potentially damaging over-rotation or hyperextension of sections of the system.

In some embodiments, an assistive device is used to place and remove a device. In some embodiments, an assistive device can lower the force required to assemble or remove a device. In some embodiments, an assistive device sequentially removes sections adjacent movable parts or structures. Sequentially removing sections can result in a more gentle removal of a device from tissue rather than in an uncomfortable and or painful process.

In some embodiments, systems include a holder for devices. In some embodiments, a holder provides a protected position for a device. In some embodiments, the holder maintains the shape of a device in a resting state, preventing stress and strain on the movable parts or structures. In some embodiments, the holder maintains the shape of a device in a resting state, preventing stress relaxation and creep within the movable parts or structures.

Also disclosed herein are specific anatomical locations for assembling conforming devices.

Also disclosed herein are specific non-tissue related locations for assembling conforming devices.

In some embodiments, a neural interface system is provided. The neural interface system can include a first neural interface device and a second neural interface device. In some embodiments, each of the first neural interface device and second neural interface device comprise at least two rigid panels, each rigid panel operably connected to an adjacent rigid panel by at least one movable structure in between adjacent rigid panels and configured to substantially conform to tissue in a first configuration and a second configuration different from the first configuration. In some embodiments, each rigid panel of both the first neural interface device and the second neural interface device comprises magnetic zones and non-magnetic zones. In some embodiments, the first neural interface device is configured to be wearable above a skin surface of a subject. In some embodiments, the second neural interface device is configured to be implantable below the skin surface of the subject. In some embodiments, the first neural interface device and the second neural interface device are configured to movably align with each other via the magnetic zones.

In some embodiments, the first device and the second device each comprise at least two magnetic zones configured to align the first device and the second device over a range of substrate contour geometries. In some embodiments, the at least one movable structure comprises a hinge. In some embodiments, the first neural interface device and the second neural interface device are configured to be in wireless communication with each other. In some embodiments, the first neural interface device and the second neural interface device are configured to be in ultra wide band (UWB) wireless communication with each other. In some embodiments, the first neural interface device and the second neural interface device comprise inductive coils configured for wireless power transmission. In some embodiments, the second neural interface device comprises at least one sensor configured to wirelessly send data. In some embodiments, the first neural interface device comprises a controller configured to wirelessly receive data from the at least one sensor. In some embodiments, the second neural interface device comprises at least one neural effector, and the controller of the first neural interface device is further configured to wirelessly send instructions to adjust parameters of the at least one neural effector based on the data from the at least one sensor.

In some embodiments, a method of positioning a neural interface system is provided. The method can include implanting a first neural interface device under a skin surface of a subject. In some embodiments, the first neural interface device comprises a plurality of rigid panels connected by at least one movable structure. In some embodiments, each rigid panel of the first neural interface device comprises a magnetic zone and a non-magnetic zone. The method can include positioning a second neural interface device on or above the skin surface of the subject. In some embodiments, the second neural interface device comprises a plurality of rigid panels connected by at least one movable structure. In some embodiments, each rigid panel of the second neural interface device comprises a magnetic zone and a non-magnetic zone. The method can include aligning the first neural interface device with the second neural interface device. In some embodiments, aligning occurs via magnetic attraction of the magnetic zones of the first neural interface device and the second neural interface device.

In some embodiments, the first neural interface device and the second neural interface device substantially conform with tissue after aligning, and as the tissue moves. In some embodiments, the second neural interface device is positioned on a location spaced apart above the skin surface of the subject. In some embodiments, the second neural interface device is positioned directly on the skin surface of the subject. In some embodiments, the method can include removing the second neural interface device from the subject by placing a removal tool comprising a plurality of magnetic zones in contact with or not in contact with, but in magnetic proximity to the magnetic zones of the plurality of rigid panels In some embodiments, the method can include withdrawing the removal tool along with the second neural interface device.

In some embodiments, a method of implanting a neural interface system is provided. The method can include positioning a neural interface device with respect to tissue at a first location under the skin of a subject, the neural interface device comprising a first rigid component spaced apart from a second rigid component comprising a magnet comprising an aperture. The method can include fixing the magnet at a second location under the skin of the subject.

In some embodiments, fixing the magnet comprises placing a screw through the aperture of the magnet into tissue. In some embodiments, fixing the magnet comprises placing a suture through the aperture of the magnet into tissue. In some embodiments, the neural interface device is fixed with respect to the tissue only via the magnet spaced apart from the neural interface device. In some embodiments, the first rigid component and the second rigid component are connected via a flexible, non-elastic backing component. In some embodiments, the method can include removing the non-elastic backing component after fixing the magnet at the second location. In some embodiments, the method can include sensing physiologic information from the neural interface device, and wirelessly transmitting the sensed physiologic information to an external device. In some embodiments, the magnet comprises a ring. In some embodiments, the magnet of the second rigid component comprises a first magnet, and the first rigid component comprises a second magnet. In some embodiments, the method can include aligning a second device on or above a skin surface of the subject with the neural interface device, the second device comprising a magnet, the magnet of the second device aligning with the magnet of the second rigid component.

In some embodiments, a neural interface system is provided. The neural interface system can include a neural interface device. The neural interface system can include a magnet comprising a ring spaced apart from the neural interface device. The neural interface system can include a flexible, non-elastic backing component connecting the neural interface device and the magnet.

In some embodiments, the neural interface device comprises a neural microarray comprising at least one electrode. In some embodiments, the electrode comprises a stimulation electrode. In some embodiments, the electrode comprises a recording electrode. In some embodiments, the neural interface device comprises at least one sensor. In some embodiments, the neural interface device comprises at least one transmitter configured to wirelessly transmit data to an external device. In some embodiments, the at least one transmitter is configured to wirelessly transmit data via an ultra-wideband (UWB) protocol. In some embodiments, the neural interface device comprises a plurality of rigid panels connected via a movable structure. In some embodiments, the neural interface device comprises at least one sensor, and the neural interface device comprises a controller configured to wireless receive data from the at least one sensor based on the data from the at least one sensor. In some embodiments, the neural interface device comprises at least one neural effector, and the controller is configured to wirelessly send instructions to adjust parameters of the at least one neural effector.

BRIEF DESCRIPTION OF THE DRAWINGS

FIG. 2 shows an isometric view of a device conforming to a curved tissue surface.

FIG. 2A shows an isometric view of a device conforming to a flat tissue surface.

FIG. 2B shows an isometric view of a device conforming to a curved tissue surface.

FIG. 3 shows an isometric view of a device conforming to a curved tissue surface.

FIG. 3A shows an isometric view of a device conforming to a flat tissue surface.

FIG. 3B shows an isometric view of a device conforming to a curved tissue surface.

FIG. 11 shows two parts of a device assembled adjacent tissue

FIG. 11A shows two parts of a device assembled adjacent tissue with one part held against the tissue by a screw.

FIG. 11B shows a device with two parts connected by a non-stretchable flexible section adjacent tissue.

DETAILED DESCRIPTION

Figure 1:
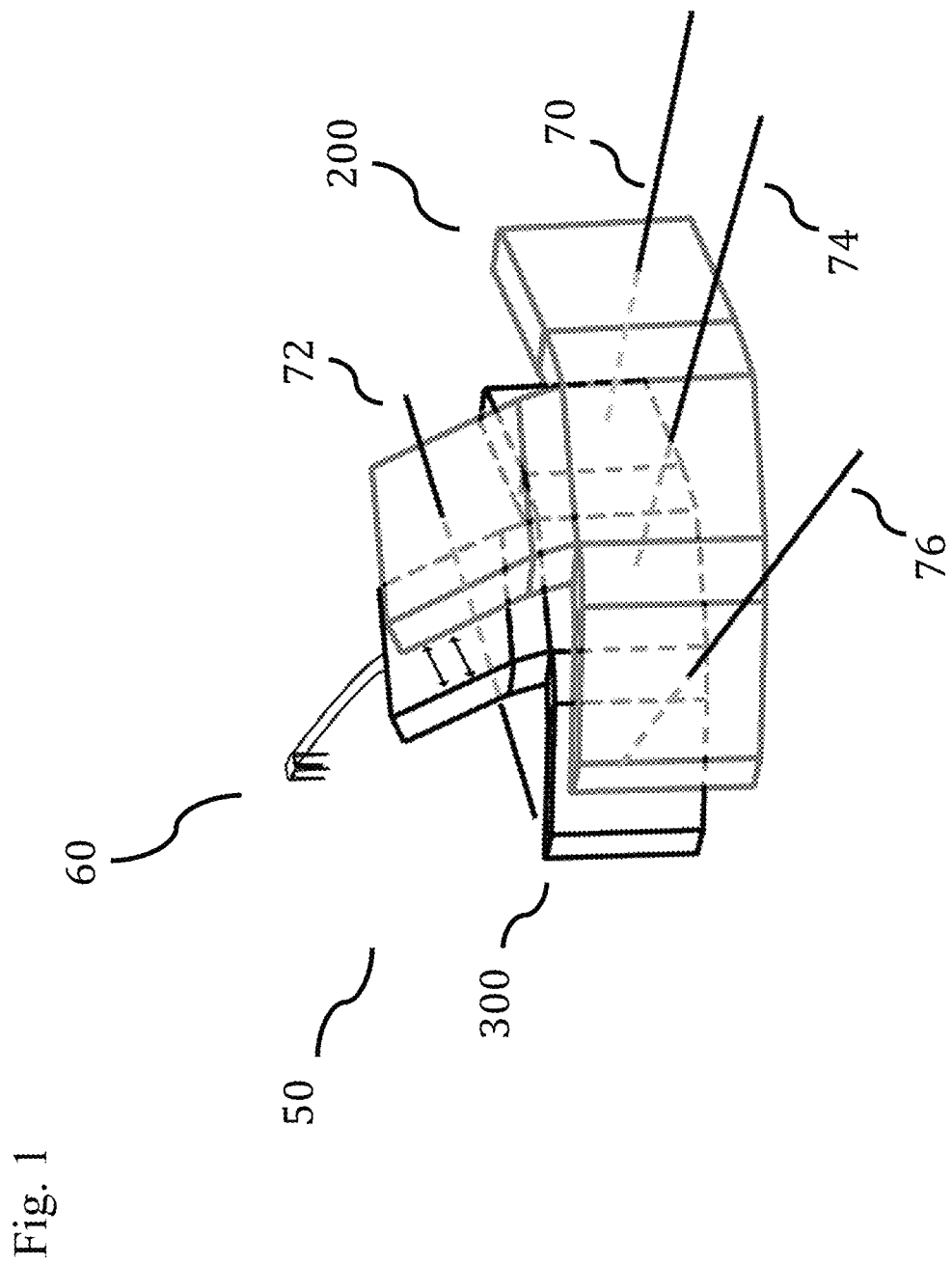
FIG. 1 shows an isometric view of a device wirelessly communicating with another device, according to some embodiments.

Biological sensors are implanted within the bodies of animals and humans to study, record, stimulate, and treat various anatomies. Typically, this occurs within animal research of a variety of fields (e.g. neurological disorders and basic nervous system function) as well as clinical diagnosis and therapy (e.g., epilepsy, tremor, and other neurological diseases).

Biological sensors are implanted for a variety of reasons, including wirelessly transmitting signals into and out of the body, through a variety of methods including radio frequency, ultrasonic, and optical transmissions. Radio frequency communication is the most pervasive form of wirelessly communicating with devices implanted within the body. It is advantageous to transmit large amounts of data into or out of the body; some non-limiting examples of this need is the recording of neurons or muscle cell firing, ion channel activity, or the sending of specific commands for stimulation or ablation. The firing of a neuron produces a distinct voltage signature over time that requires a detailed analog recording to identify. These analog recordings over long periods of time require large amounts of data to be recorded and transmitted. Transmitting at a high total data rate out of the body is advantageous as it increases the number of neuron firing events that can be identified over time.

Unfortunately, wireless transmissions are attenuated by tissue, limiting the amount of data transmitted between an implanted device and external devices. Attempts to work around this challenge are problematic and include increasing the number of implanted devices, as well as reducing tissue thicknesses to reduce signal attenuation. Reducing tissue thicknesses is time consuming during surgery and damaging or irreversible for most organisms. Increasing the number of implanted devices has proven difficult due to wireless transmissions of individual implants disrupting one another. Increasing the number of implants also increases the invasiveness of the procedure and device, increasing the risk of unsuccessful results for the implant due to infection or other surgical complications. Another significant challenge for implanted devices is providing them with power. Powering a dispersed network of implants provides many additional challenges to systems, and connecting nodes of an implant network with cables to a single power source increases the difficulty and delicacy of implantation and aides the spread of infection from one area to another within a body. Alignment of external components with implanted antennas can also be challenging. These limitations prevent the implantation of wireless chronic neural interfaces in a wide variety of situations. This reduces the amount of data acquired, limiting the study of anatomy, and ultimately limits current and future therapies.

Accordingly, in some embodiments, disclosed herein are wireless systems that increase the amount of data that can be transmitted into and out of the body within compact systems. In some embodiments, the system may include one or more antennas operating on the same or overlapping frequency spectrum arranged in a shielded array to prevent interference with one another while increasing the total amount of data transmitted into and out of the body. It can also be advantageous to place arrays in the body in areas with thinner tissue; in one embodiment, this may be the scalp. In some embodiments, the antenna arrays may be configured with at least one other antenna operating on another frequency spectrum. As an example, this would enable one frequency for communicating with basic functions of an implanted device and another frequency spectrum for transmitting large amounts of information into and out of the body. In some embodiments, the antenna arrays communicate using Ultra-wideband (UWB). Ultra-wideband uses low energy for short-range, high-bandwidth communications over a large portion of the radio spectrum. Ultra-wideband can transmit information spread over a large bandwidth at levels equal to or greater than 500 MHz or 20% of fractional bandwidth. Ultra-wideband can be operable between 3.1 GHz and 10.6 GHz within plus or minus 0.1 GHz. In some embodiments, wireless communication can occur at a data rate between, for example, 1 kbps and 50 Gbps, such as no more than about 50 Mbps, 100 Mbps, 200 Mbps, 300 Mbps, 400 Mbps, 500 Mbps, 1 Gbps, 10 Gbps, 20 Gbps, 25 Gbps, 30 Gbps, or 40 Gbps, or ranges including any two of the foregoing values. Ultra-wideband can be advantageous within medical device applications because it transmits large amounts of data while requiring low levels of power, reducing the power requirements and maximum temperatures of implanted devices. Ultra-wideband can also be advantageous within medical device applications as its large bandwidth is more resistant to interference than narrow band transmissions. In some embodiments, antennas within the device system are capable of operating, within plus or minus 5%, at frequencies between 6.765 MHz and 6.795 MHz, 13.553 MHz and 13.567 MHz, 26.957 MHz and 27.283 MHz, 40.66 MHz and 40.7 MHz, 433.05 MHz and 434.79 MHz, 902 MHz and 928 MHz, 24 GHz and 24.25 GHz, 61 GHz and 61.5 GHz, 122 GHz and 123 GHz, 244 GHz and 246 GHz, 401 MHz and 401.85 MHz, 401.85 MHz and 402 MHz, 402 MHz and 405 MHz, 405 MHz and 406 MHz, 413 MHz and 419 MHz, 426 MHz and 432 MHz, 438 MHz and 444 MHz, or 451 MHz and 457 MHz, or ranges including any two of the foregoing values.

In some embodiments, tissue can be altered to increase the strength or reduce attenuation of wireless communication between devices. In other embodiments, tissue can be altered for positioning of a device that increases the strength or reduces attenuation of wireless communication with another device. In some embodiments, the tissue is a component of the wireless device as it alters the performance based on its thickness and density. The wireless systems' performance is affected by its integration with tissue. The tissue thickness, alignment of implanted and external antennas and the distance between implanted and external antennas, contributes to reliable communication and electromagnetic radiation emitted through tissue not contained by the systems. Designing the wireless systems for specific tissue thicknesses and anatomical locations can increase the system performance, and limits the electromagnetic radiation emitted through tissue outside the body. Limiting the electromagnetic radiation emitted through tissue outside the body and the systems can in some cases increase safety, reduces the possibility of interference with other wireless devices, and satisfies the requirements of regulatory organizations. In some embodiments, the system can be designed and configured for head tissue thicknesses of 5 mm to 25 mm, such as no more than about 6 mm, 7 mm, 8 mm, 9 mm, 10 mm, 11 mm, 12 mm, 13 mm, 14, mm, 15 mm, 17 mm, 19 mm, 21 mm, or 24 mm. In still other embodiments, the system can be designed and configured for tissue thicknesses of 1 mm to 5 mm, such as no more than about 2 mm, 3 mm, or 4 mm. In some other embodiments, the system can be designed for tissue thicknesses of 25 mm to 45 mm, such as no more than about 28 mm, 32 mm, 36 mm, 40 mm, or 44 mm.

In some embodiments, disclosed herein are systems that can integrate with various types of neural interfaces that act as recording or stimulation electrodes, optical fibers, or as hollow tubes for media, e.g., fluid delivery. In still other embodiments, advantageous configurations for various treatment modalities including recording, stimulating, magnetic stimulation, magnetic monitoring, fluid delivery, temperature control, optical stimulation, optical monitoring, video monitoring, and chemical irrigation of neural tissue. In some embodiments, the systems and methods can be utilized to monitor nerve firing to locate nerves, such as parasympathetic, sympathetic, afferent, and/or efferent nerves prior to or during a denervation proceeding, such as renal denervation, a cardiac EP study, vagal nerve ablation, and the like.

In some embodiments, the systems can also serve as a delivery device for a therapeutic agent including a drug, such as an antithrombotic agent, an antibiotic, an anti-inflammatory, an anti-epileptic, viral vectors, a chemotherapeutic agent, for example, or combinations thereof. The therapeutic agent could also include one or more growth factors, agonists or antagonists, or stem cells, for example. In some embodiments, the systems can be implanted within any tissue within the body dependent upon the desired research or clinical result; including nervous, muscle, connective, epithelial, cardiac, lung, renal, gastrointestinal, and bone tissues.

Neuroscientists and clinicians may need devices that monitor and treat nervous systems and other biological tissues from implanted and external positions. These devices may need to adapt and conform to the spectrum of complex three-dimensional surfaces of tissues. These shapes can include approximately concave, approximately flat, and approximately convex, as well as many other three-dimensional shapes.

Neuroscientists and clinicians have a well-recognized need to wirelessly communicate with large groups of neurons and transmit wireless power through tissue. Available research devices struggle to demonstrate reliable wireless transmission of data and power.

Neural interface devices are inserted into tissue and assembled to tissue in a variety of ways including mechanical insertion, suturing to tissue, adhesive based assembly, and the use of magnetic materials. The most pervasive forms of assembly are the removal of bone, screwing of implanted devices into place, and the holding in place of devices external to the body by magnetic force. Maintaining external assembly of a device to a body requires a balance between a strong enough magnetic force of attraction, a low enough pressure applied to the skin to avoid skin breakdown or ulceration, and the conformance of the device to the shape of the body to mechanically engage with it. Maintaining a close proximity and alignment between radio antennas and inductive coils adjacent tissue is a significant need of researchers. Currently available devices are assembled in relatively flat sections of tissue. Devices assembled to flat sections of tissue are more susceptible to dislodgment by shear forces than when assembled to three-dimensionally curved sections of tissue, which provide a mechanical engagement in one or more directions for the device.

Unfortunately, there are limited devices available that can wirelessly communicate data about the nervous system from beneath the skin, leading to a reliance on devices that protrude through the skin. The devices that are available for implantation under the skin either have a limited ability to record or stimulate the nervous system and thus are small in nature, or, are large, bulky, and do not confirm to tissue within or outside of the body. The variations in thickness of tissue and the movement of tissue pose significant challenges to maintaining alignment and proximity of antennas and inductive coils for assembled devices.

These limitations prevent the implantation of chronic neural interfaces in a wide variety of situations. This reduces the amount of data acquired as well as limiting current and future therapies.

Accordingly, in some embodiments, disclosed herein are systems and devices that provide unlimited degrees of freedom for placing, stabilizing, and removing devices that conform to the nervous system and other tissues.

In some embodiments, the systems or an individual device can interface with the nervous system to diagnosis and/or treat epilepsy, a movement disorder (e.g., Parkinson's Disease), a psychiatric disorder (e.g., clinical depression), the result of a stroke, Alzheimer's disease, a cognitive disorder, an anxiety disorder, an eating disorder, an addition or craving, restless leg syndrome, a sleep disorder, Tourette's syndrome, a stress disorder, coma, autism, a hearing disorder, a vision disorder, blindness, retinal degeneration, age related macular degeneration, cortical injury, optic nerve injury, dry eye syndrome, a speech disorder, amblyopia, headaches, temporomandibular joint disorder, pain (e.g., phantom limb pain and chronic pain), urinary incontinence, erectile dysfunction, bone disease, arthritis, tendonitis, the result of ligament or tendon damage, and paralysis (e.g., facial nerve paralysis and spinal paralysis). In some embodiments, the systems or an individual device can be used to provide control of a prosthetic such as a limb or an external computer.

In some embodiments, the systems or an individual device may wirelessly communicate with a system that is connected to a network or cloud of data. In other embodiments, the systems can be connected to a biological interface to monitor tissue. In some other embodiments, the systems are connected to a biological interface to modulate tissue. In still other embodiments, the systems are connected to a biological interface to monitor and modulate tissue. In other embodiments, the biological interface can include an implantable camera, and/or other sensors including EEG, EMG, ECG, PPG, HRV, motion, and/or other sensors.

In other embodiments, the systems or an individual device can study, diagnose, and/or treat cardiovascular conditions such as heart failure, rheumatic heart disease, hypertensive heart disease, ischemic heart disease, angina, coronary artery disease, cerebral vascular disease, stroke, atherosclerosis, cerebrovascular disease, cardiomyopathy, pericardial disease, valvular heart disease, inflammatory heart disease, congenital heart disease, and peripheral arterial disease.

In still other embodiments, the systems or an individual device can study, diagnose, and/or treat cancers, including leukemia, lymphoma, myeloma, bladder cancer, lung cancer, brain cancer, melanoma, breast cancer, non-Hodgkin lymphoma, cervical cancer, and ovarian cancer.

In other embodiments, the systems or an individual device can study, diagnose, and/or treat type 1 and type 2 diabetes, or metabolic syndrome. In some embodiments, the systems can include a biological interface to study, diagnose, and/or treat orthopedic conditions, including osteoarthritis, rheumatoid arthritis, bone fractures, lower back pain, neck pain, and a herniated disk.

In other embodiments, the systems or an individual device can study, diagnose, and/or treat eye conditions, including glaucoma, cataracts, age-related macular degeneration, amblyopia, diabetic retinopathy, retinal detachment, retinal tearing, and dry eye syndrome.

In still other embodiments, the systems or an individual device can study, diagnose, and/or treat hearing conditions, including hearing loss, Meniere's disease, malformation of the inner ear, autoimmune inner ear disease, tinnitus, and vertigo.

In other embodiments, the systems or an individual device can study, diagnose, and/or treat tactile disorders, including impaired sensitivity to pressure applied to the skin, elevated two-point discrimination thresholds (i.e. impaired spatial acuity), loss of vibratory sense, and deficits in proprioception.

In other embodiments, the systems or an individual device can study, diagnose, and/or treat taste, taste impairing conditions, smell, and smell impairing conditions.

In still other embodiments, the systems can be movably engaged within one, two, or more body tissues, regions, or organ systems including but not limited to the scalp, skin, muscle, bone, neural tissue, heart, lungs, trachea, bronchi, diaphragm, liver, pancreas, kidneys, bladder, urethra, spleen, esophagus, stomach, intestine, penis, testes, uterus, or ovary.

In some embodiments, provided is a closed loop control system for stimulating (or ablating) and monitoring neural activity. In some embodiments, systems and methods as disclosed herein can modulate neural tissue, and have a stimulatory or inhibitory effect. The effect can be detected by one or more physiologic sensors, which transmit signals to a processor, which can in turn adjust the modulation of neural tissue depending on the detected signals. Neural tissue is specialized for the conduction of electrical impulses that convey information or instructions from one region of the body to another. About 98% of neural tissue is concentrated in the brain and spinal cord, which are the control centers for the nervous system. Neurons transmit signals as electrical charges which affect their cell membranes. A neuron has a cell body (soma) that contains a nucleus. The stimulus that results in the production of an electrical impulse usually affects the cell membrane of one of the dendrites, which then eventually travels along the length of an axon, which can be a meter long. Axons are often called nerve fibers with each ending at a synaptic terminal. Neuroglia are cells of the CNS (central nervous system) and PNS (peripheral nervous system) that support and protect the neurons. They provide the physical support for neural tissue by forming myelin sheaths, as well as maintaining the chemical composition of the tissue fluids and defending the tissue from infection. Schwann cells are specialized PNS cells that form myelin sheaths around neurons. Neurons (nerve cell) include a cell body that contains the nucleus and regulates the functioning of the neuron. Neurons also include axons that are cellular process (extension) that carry impulses away from the cell body. Neurons also include dendrites that are cellular process (extension) that carry impulses toward the cell body. A synapse is a space between axon of one neuron and the dendrite or cell body of the next neuron—transmits impulses from one neuron to the others. Neurotransmitters are chemicals released by axons and transmit impulses across synapses.

In still other embodiments, provided is a closed loop control system for stimulating and monitoring physiological activity. In other embodiments, systems and methods as disclosed herein can modulate tissue and organs, and have a stimulatory or inhibitory effect. The effect can be detected by one or more physiologic sensors, which transmit signals to a processor, which can in turn adjust the modulation of neural tissue depending on the detected signals. A system could include a first antenna or pair of antennas configured for stimulation only, and a second antenna or pair of antennas configured for recording only. The first and second pair of antennas can operate at high data rates, and can advantageously obviate the need for large amounts of bidirectional communication from each individual antenna/pairs of antennas. The pair of antennas exclusively or substantially entirely dedicated to recording can send signals out of the body (or to another location within the body), while the pair of antennas exclusively or substantially entirely dedicated to stimulation can send signals to stimulate electrodes, end effectors delivering RF, microwave, electromagnetic, ultrasound, thermal, cryo, and/or other energy, fluid, etc. to antennas within the body or external to the body. Relegating the primary data stream of each pair to unidirectional only can allow for reduced overhead in wireless transmission, increasing the data rate available and a more robust closed loop control system for better control over the neural circuitry being modulated. This can advantageously allow for wireless closed loop control at high channel counts/data rates. In some embodiments, the system can be configured to record and/or stimulate about or at least about 100, 150, 250, 500, 1,000, 5,000, 10,000, 100,000, 500,000, 1,000,000 channels, or even more.

In some embodiments, microfilaments are used to record and stimulate neural tissue. In still other embodiments, it is advantageous that the approximate diameter of circular microfilaments for conducting electrical current is between 1 µm and 250 µm, such as no more than about 25 µm, 50 µm, or 75 µm. For electrical stimulation, larger sites up to 50 µm would be advantageous to achieve surface areas that meet useful stimulation current requirements without a coating. The approximate diameter of circular microfilaments for conducting or monitoring light is between is 0.1 µm to 250 µm, such as no more than about 25 µm, 50 µm, or 75 µm. The approximate diameter of circular microfilament tubes for delivering or circulating gases, fluids, and mixtures in some embodiments is between 1 µm to 100 µm, or no more than about 50 µm, 75 µm, 100 µm, or 150 µm. Microfilaments can also be placed within a packed geometry that allows for a tapering of the penetrating area cross sections to reduce the cross sectional area and thus long term adverse neural tissue response. In some embodiments, the microfilaments can extend outward from the body's surface; these sites can be formed (e.g., bent or flattened) to provide desired functional characteristics.

A microfilament array body can take multiple forms including penetrating structures with microfilament sites and joining sections to optimize placement within the nervous system. An approximate cross sectional area of a penetrating array body in some embodiments is 1 µm² to 0.2 mm², preferably up to approximately 7850 µm² or even more. For large area coverage as in electrocorticography, larger body areas up to approximately 100 cm² or more would be advantageous to collect more data from the outer surface of a neural tissue section. Systems and methods as disclosed herein can be used or modified for use with neural arrays as disclosed, for example, in U.S. Pat. No. 9,095,267 to Halpern et al., which is hereby incorporated by reference in its entirety.

In some embodiments, the systems are movably assembled within a sealed connector assembly. In still other embodiments, the connector is movably assembled to another connector containing the wireless systems. In some embodiments, the wireless systems embedded in a connector assembly might be advantageous underwater, in corrosive environments, in low-visibility environments, in outer space, and in applications requiring a low force of connection. In other embodiments, the systems embedded within a wireless connector would be advantageous in blood, urine, hormones, and lymph. In still other embodiments, the systems would be advantageous in environments that limit the use of hands, including industrial, athletic, and military pursuits.

One advantage of an implantable wireless device in some embodiments is the wide range of materials and components available to improve implantation conditions and long term performance of a device within a nervous system. The components of the device can be formed from titanium, niobium, gold, platinum, platinum iridium, carbon, stainless steel, steel, aluminum, conductive polymers, polymers, ceramics, organic materials, combinations of the foregoing, or any other materials.

In some embodiments, provided is a closed loop control system for stimulating and monitoring neural activity. To meet this objective, microfilaments are embedded in various body configurations with six degrees of freedom to provide many system options for interacting with neural tissue. As an example, this would enable the data collected from an implanted device (or external source) to help guide the output of a second stimulating device.

In some embodiments, devices are deployed in target substrates other than tissue (e.g., spaced apart from the patient's skin), such as submerged in water or soil. In other embodiments the devices are contained within vessels such as pipes, spacecraft, automobiles, airplanes, tires, concrete, flooring, walls, roofs, and roadways. In some embodiments, the devices are contained within clothing or accessories, such as shoes, gloves, skull caps or other headwear, bags, sleeves, stockings, blankets, shirts, pants, belts, pillow cases, chin straps, assistive devices (e.g., canes, walkers, wheelchairs, etc.) and furniture. In some embodiments, the devices are connected, such as attached, to a subject's hair.

FIG. 1 shows an isometric view of a system 50 including a distal device 300 and a proximal device 200 with orthogonal axis 70, axis 72, axis 74, and axis 76. In some embodiments, the axes of the proximal device 200 are aligned with the axes of the distal device 300. In other embodiments, the orthogonal axes of the distal device 300 and the orthogonal axes of the proximal device 200 are aligned for example, between about 0.10 and 10°, such as no more than about 1°, 2°, 3°, 4°, 5°, 6°, 7° 8°, 9° or 102, or ranges incorporating any two of the aforementioned values. In other embodiments, the orthogonal axes of the distal device 300 and the orthogonal axes of the proximal device 200 are aligned for example, between about 10 and 180°, such as no more than about 30°, 60°, 90°, 120°, or 150°. In some embodiments, distal device 300 is movably assembled to an electrode 60. In some embodiments, proximal device 200 is movably assembled to an electrode. In some embodiments, the distal device 300 is implanted within the body, and the proximal device 200 is external to the body. In some embodiments, the proximal device 200 includes panels that are thicker relative to panels of the distal device 300, such as at least about 5%, 10%, 15%, 20%, 25%, 30%, 35%, 40%, 45%, 50%, 75%, 100%, or more thicker, or ranges including any two of the foregoing values. While the thickness of one device can be different from the thickness of another device in some embodiments, the first device can still have the same outer perimeter of the second device in some cases. In some embodiments, the magnetic zones determine the outermost zones of a first device and a second device. In some embodiments, the proximal device 200 includes adjustable straps configured to provide adjustment for alignment elements, e.g., magnets or other elements such as disclosed herein, and to facilitate alignment with complementary alignment elements connected to the distal device 300. In some embodiments, a distal device 300 includes one or no flexible sections (e.g., movable structures) and a proximal device 200 can include two or more flexible sections (e.g., movable structures) to better conform to variable anatomy (e.g., changes in anatomy over the skin, clothing, or accessories for example). In some embodiments, one, two, or more alignment elements such as magnets can be encased within a monolithic implant (e.g., distal device 300) with no movable or other flexible structures, or no more than a single movable or flexible structure.

FIG. 2 shows an isometric view of a device 100 conforming to a relatively convex tissue surface 40. In some embodiments, the device 100 has a first movable part or structure 140 and a second movable part or structure 120. In some embodiments, the rigid panels 105, 110, and 115, are movable with respect to each other to allow the body to move between a displaced state and a non-displaced state. As shown, the device 100 can include a central panel 110 operably connected to lateral panels 105, 115 via respective movable structures 140, 120. In some embodiments, the device 100 substantially conforms to tissue surface 40 by displacing around movable part or structure 140 and or movable part or structure 120. In some embodiments, device 100 can have a length of for example, between about 1 cm and 10 cm, such as no more than about 2 cm, 4 cm, 6 cm, 8 cm, or 10 cm. In some embodiments, device 100 can have a length of for example, between about 10 cm and 200 cm, such as no more than about 20 cm, 50 cm, 100 cm, 150 cm, or 180 cm. In some embodiments, a rigid panel of device 100 can have a length of for example, between about 0.5 cm and 5 cm, such as no more than about 1 cm, 2 cm, 3 cm, 4 cm, or 5 cm. In some embodiments, a rigid panel of device 100 can have a width of for example, between about 0.5 cm and 5 cm, such as no more than about 1 cm, 2 cm, 3 cm, 4 cm, or 5 cm. In some embodiments, device 100 can have a thickness of for example, between about 0.1 cm and 1.0 cm, such as no more than about 0.1 cm, 0.2 cm, 0.3 cm, 0.4 cm, 0.5 cm, 0.7 cm, 0.8 cm, or 1.0 cm. In some embodiments, a rigid panel of device 100 can have a thickness of for example, between about 0.01 cm and 0.1 cm, such as no more than about 0.01 cm, 0.02 cm, 0.05 cm, 0.07 cm, 0.08 cm or 0.1 cm. In some embodiments, a movable structure between panels of device 100 can have a thickness of for example, between about 0.1 cm and 1.0 cm, such as no more than about 0.1 cm, 0.2 cm, 0.3 cm, 0.4 cm, 0.5 cm, 0.8, 0.9, or 1.0 cm. In some embodiments, a movable structure between panels of device 100 can have a thickness of for example, between about 0.01 cm and 0.1 cm, such as no more than about 0.01 cm, 0.02 cm, 0.05 cm, 0.07 cm, 0.08 cm or 0.1 cm. In some embodiments, a systems and an individual device can have one, two, or more movable parts or structures aligned orthogonally to other movable parts or structures. In some embodiments, a systems can include one or more movable parts or structures aligned for example, between about five and ninety degrees to one another. In some embodiments, a device can contain a central component with mounting positions for movable parts or structures. The central component can have multiple movable parts or structures assembled to it dependent upon the desired research or clinical purpose. In some embodiments, devices are positioned to align the movable parts or structures of each device. In some embodiments, the movable parts or structures of devices are not aligned. In some embodiments, aligned devices have the same number of movable parts or structures. In other embodiments, aligned devices have different numbers of movable parts or structures. In some embodiments, the devices have approximately matching movable parts or structures. In some embodiments, the devices do not have matching movable parts or structures. In some embodiments, devices are positioned to align the movable parts or structures of each device. In some embodiments, devices are positioned without the alignment of the movable parts or structures. In some embodiments, some panels can have flat or substantially flat surfaces. In some embodiments, some panels can have microstructures to increase the surface area of the panel for improved efficacy of an effector, such as a stimulating electrode for example. In some embodiments, a device could include 2, 3, 4, 5, 6, 7, 8, 9, 10, 15, 20, 25, 30, 35, 40, 45, 50, 60, 70, 80, 90, 100, 150, 200, 300, 400, 500, or more panels, or ranges including any two of the foregoing. Relatively large numbers of panels, each panel directly connected to one or more movable structures in some embodiments, may provide improved conformance to, for example, organs with complex geometries. In some embodiments, a movable structure of a device can have a length of for example, between about 1 cm and 10 cm, such as no more than about 2 cm, 4 cm, 6 cm, 8 cm, or 10 cm, or ranges including any two of the foregoing values. In some embodiments, a movable structure of device 100 can have a length of for example, between about 10 cm and 200 cm, such as no more than about 20 cm, 50 cm, 100 cm, 150 cm, or 180 cm, or ranges including any two of the foregoing values.

FIG. 2A shows an isometric view of a device 100 conforming to a substantially flat tissue surface 42. In some embodiments, the device 100 has a movable part or structure 140 and a movable part or structure 120. In some embodiments, the device 100 conforms to tissue surface 42 by displacing around movable part or structure 140 and or movable part or structure 120.

FIG. 2B shows an isometric view of a device 100 conforming to a relatively concave tissue surface 44. In some embodiments, the device 100 has a movable part or structure 140 and a movable part or structure 120. In some embodiments, the device 100 conforms to tissue surface 44 by displacing around movable part or structure 140 and or movable part or structure 120.

FIG. 3 shows an isometric view of a device 200 conforming to an exterior of an arcuate (e.g., hemispherical or dome-like) tissue surface 50. In some embodiments, device 200 includes movable parts or structures 220, 240, and 260. In some embodiments, the rigid panels 205, 210, and 215, are movable with respect to each other to allow the body to move between a displaced state and a non-displaced state, and are each connected on different sides of rigid panel 208, with panels 210, 215 being positioned on lateral sides of panel 208 and panel 205 positioned on a side of panel 208 orthogonal to panels 210, 215 to form a "T" shape. Other shapes, including symmetric and asymmetric cross-shaped panel arrays, linear panel arrays, etc. are also possible. In some embodiments, the device 200 conforms to tissue surface 50 by displacing around one or more of the movable parts or structures 220, 240, and 260. In some embodiments, a panel 208 can be connected to other panels via movable structures on exactly, at least, or no more than about one, two, three, or all four sides of the panel 208. In some embodiments, panels can be square or rectangular as shown, although triangular, trapezoidal, pentagonal, hexagonal, heptagonal, rhomboidal, octagonal, or other shaped panels can be utilized depending on the desired clinical result. The panels can be of uniform shape, or different shapes in other embodiments.

FIG. 3A shows an isometric view of a device 200 conforming to a tissue surface 52. In some embodiments, device 200 includes movable parts or structures 220, 240, and 260. In some embodiments, the device 200 conforms to tissue surface 52 by displacing around one or more of the movable parts or structures 220, 240, and 260.

FIG. 3B shows an isometric view of a device 200 conforming to the interior of an arcuate (e.g., bowl-shaped) tissue surface 54. In some embodiments, device 200 includes movable parts or structures 220, 240, and 260. In some embodiments, the device 200 conforms to tissue surface 54 by displacing around one or more of the movable parts or structures 220, 240, and 260.

Figure 4:
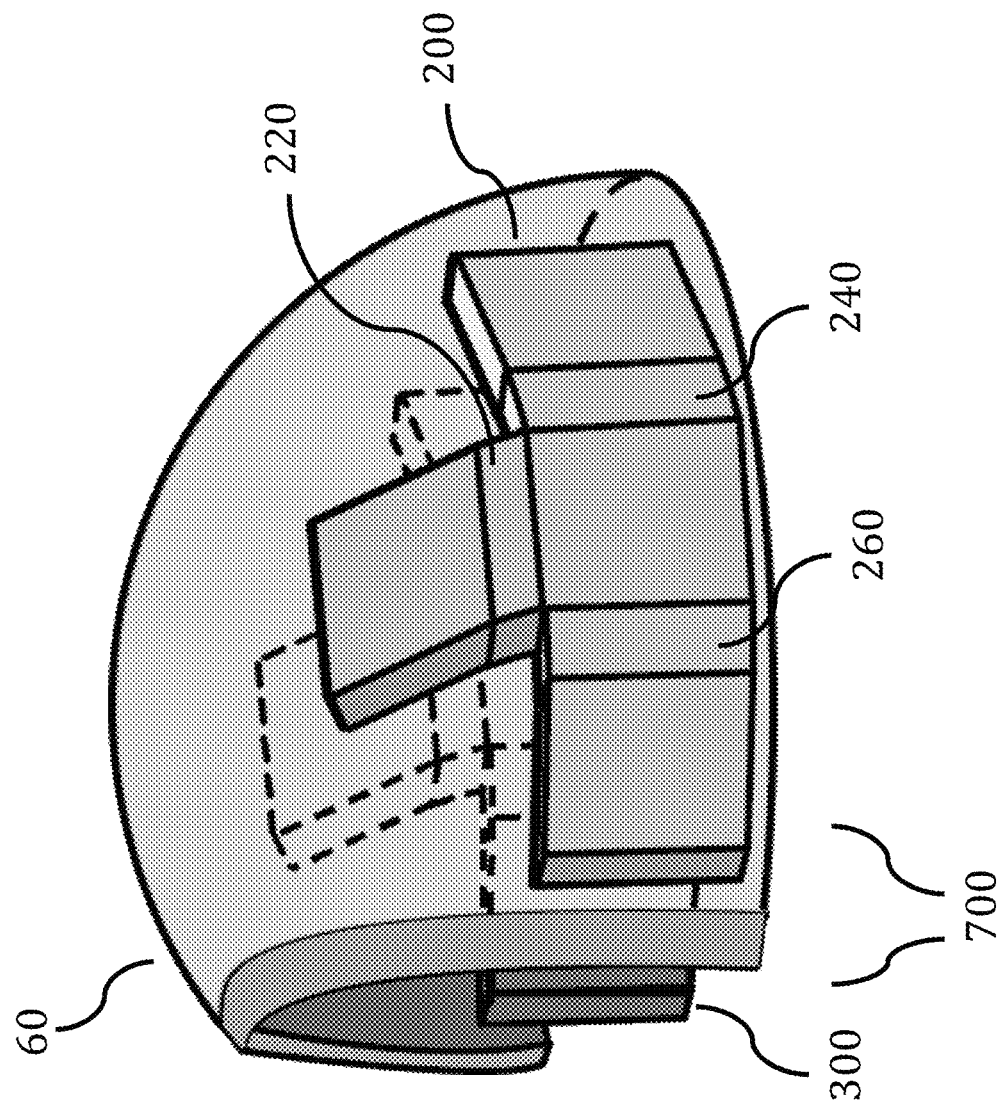
FIG. 4 shows an isometric view of two devices assembled adjacent tissue that is shown with a partial cross section.

FIG. 4 shows an isometric view of a systems 700 positioned adjacent tissue 60. In some embodiments, system 700 includes device 200 and device 300. In some embodiments, device 200 and device 300 conform to tissue 60, and can be on opposing sides of the tissue as illustrated. In some embodiments, device 200 conforms to tissue 60 by displacing around movable parts or structures 220, 240, and 260. In some embodiments, the device 300 conforms to tissue 60 by displacing around the movable parts or structures. In some embodiments, the conforming of device 200 and device 300 allows for electronics and mechanisms to align with one another, including wireless antennas, inductive power coils, or heat sinks. In some embodiments, performance and efficiency is increased by aligning wireless antennas, inductive power coils, or heat sinks.

Figure 4A:
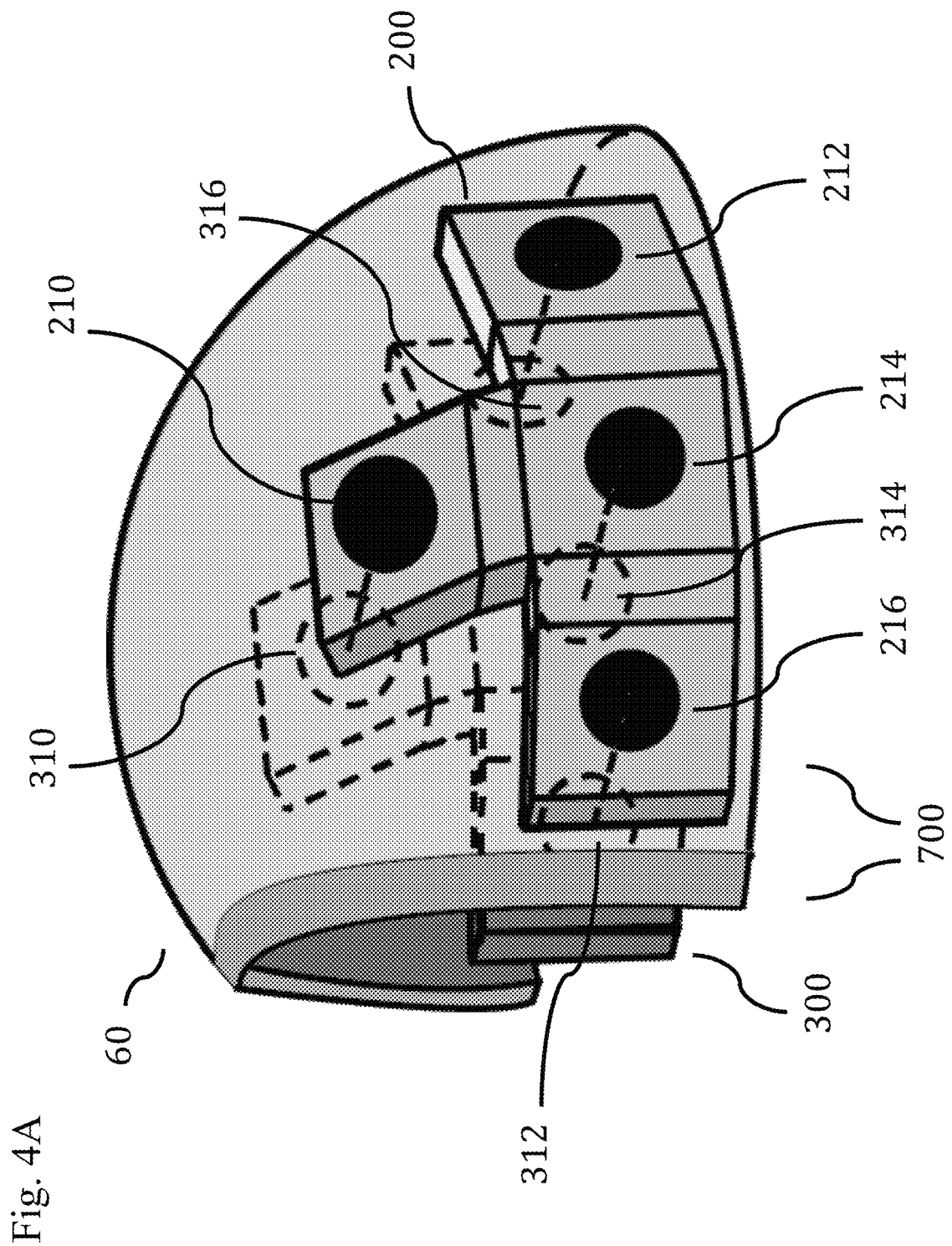
FIG. 4A shows an isometric view of two devices containing magnetic materials assembled adjacent tissue that is shown with a partial cross section.

FIG. 4A shows an isometric view of a system 700 positioned adjacent tissue 60, similar to as shown in FIG. 4. In some embodiments, system 700 includes device 200 and device 300. In some embodiments, device 200 and device 300 conform to tissue 60. In some embodiments, device 200 conforms to tissue 60 by displacing around movable parts or structures 220, 240, and 260. In some embodiments, the device 300 conforms to tissue 60 by displacing around the movable parts or structures. In some embodiments, the conforming of device 200 and device 300 occurs at least in part by magnetic material zones. In some embodiments, magnetic material zones 210, 212, 214, and 216 position device 200 using magnetic attraction to one or more nearby magnetic materials. In some embodiments, magnetic material zones 310, 312, 314, and 316 position device 300 using magnetic attraction to one or more nearby magnetic materials. In still other embodiments, magnetic material zones 210, 212, 214, and 216 position device 200 using magnetic attraction to magnetic material zones 310, 312, 314, and 316 within device 300. In some embodiments, magnetic material zones 310, 312, 314, and 316 position device 300 using magnetic attraction to magnetic material zones 210, 212, 214, and 216 within device 200. In some embodiments, the force of magnetic attraction between magnetic material zones is for example, between about 0.1 kg and about 25 kg, but no more than about 1 kg, 5 kg, 7 kg, 10 kg, 12 kg, 15 kg, 20 kg, 25 kg, 30 kg, 35 kg, 40 kg, 45 kg, 50 kg, 55 kg, 60 kg, 65 kg, 70 kg, 75 kg, 100 kg, or ranges including any two of the foregoing values. In some embodiments, the thickness of tissue 60 between device 200 and device 300 is for example, between about 1 mm and 25 mm, such as but no more than about 5 mm, 10 mm, 15 mm, and 20 mm. In some embodiments, the thickness of tissue 60 between device 200 and device 300 is for example, between about 30 mm and 100 mm, such as but no more than about 40 mm, 50 mm, 60 mm, 70 mm, 80 mm, and 90 mm. In some embodiments, the thickness of tissue 60 between magnetic material zones and nearby magnetic materials is for example, between about 1 mm and 25 mm, such as but no more than about 5 mm, 10 mm, 15 mm, and 20 mm. In some embodiments, the thickness of tissue 60 between magnetic material zones and nearby magnetic materials is for example, between about 30 mm and 100 mm, such as but no more than about 40 mm, 50 mm, 60 mm, 70 mm, 80 mm, and 90 mm. In some embodiments, magnetic material zones contain magnets, or neodymium magnets, or steel, or a ferrous composite material, or any other magnetic material. In some embodiments, the areas adjacent magnetic material zones are shaped to reduce the pressure applied to the tissue 60. The magnetic material zones can comprise only part and not the entire device 200, 300 in some embodiments. In some embodiments pressure reduction is accomplished by increasing the area of device 200 and/or device 300 in contact with the tissue 60. In other embodiments, pressure reduction is accomplished with a flexible material. In still other embodiments, pressure reduction is accomplished with intricate surface geometry that compresses the skin, and spreads pressure across the skin. In some embodiments, the magnetic forces from magnetic materials within a device compress and reduce the thickness of adjacent tissue. In some embodiments, the magnetic force between one or more magnetic material zones in one device, and one or more magnetic material zones in another device compress and reduce the thickness of adjacent tissue. In still other embodiments, the magnetic force between one or more magnetic material zones in one device, and magnetic materials compress and reduce the thickness of adjacent tissue. In some embodiments, a system can compress tissue for example, between about 0.1 mm and about 2 mm, such as no more than about 0.5 mm, 1 mm, 1.5 mm, or 2.0 mm. In some embodiments, a device can compress tissue for example, between about 0.1 mm and 2 mm, such as no more than about 0.5 mm, 1 mm, 1.5 mm, or 2.0 mm.

Figure 5:
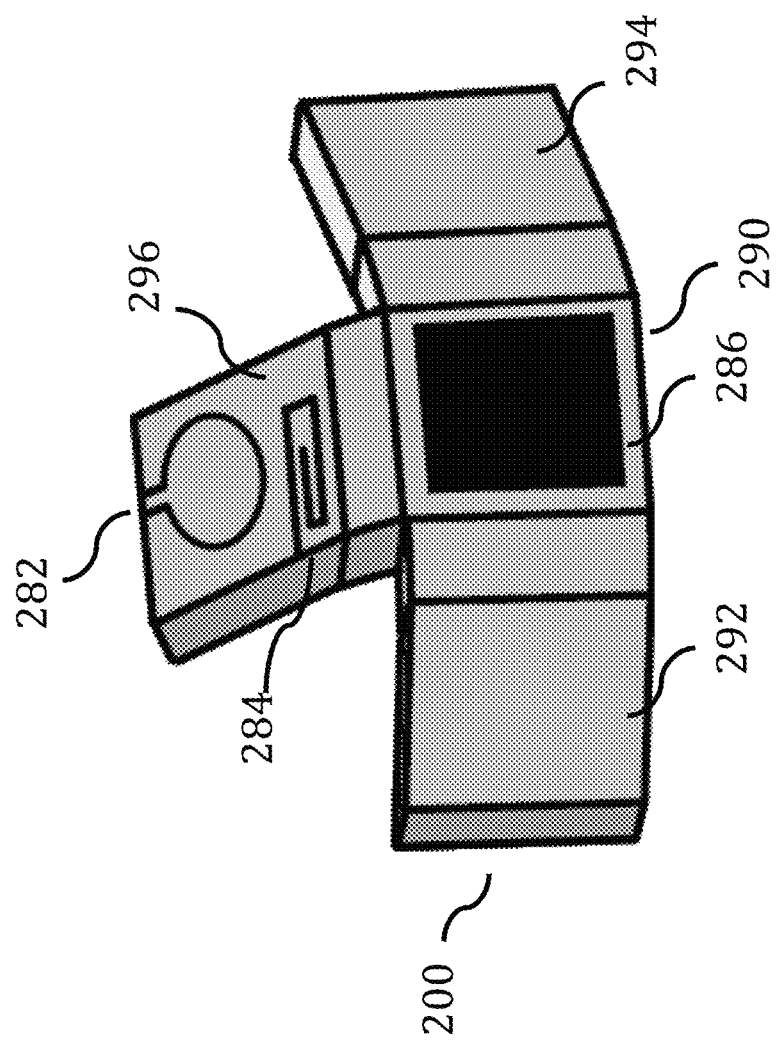
FIGS. 5-5B shows an isometric view of a device containing an inductive power coil, a radio frequency antenna, and a battery.
Figure 5A:
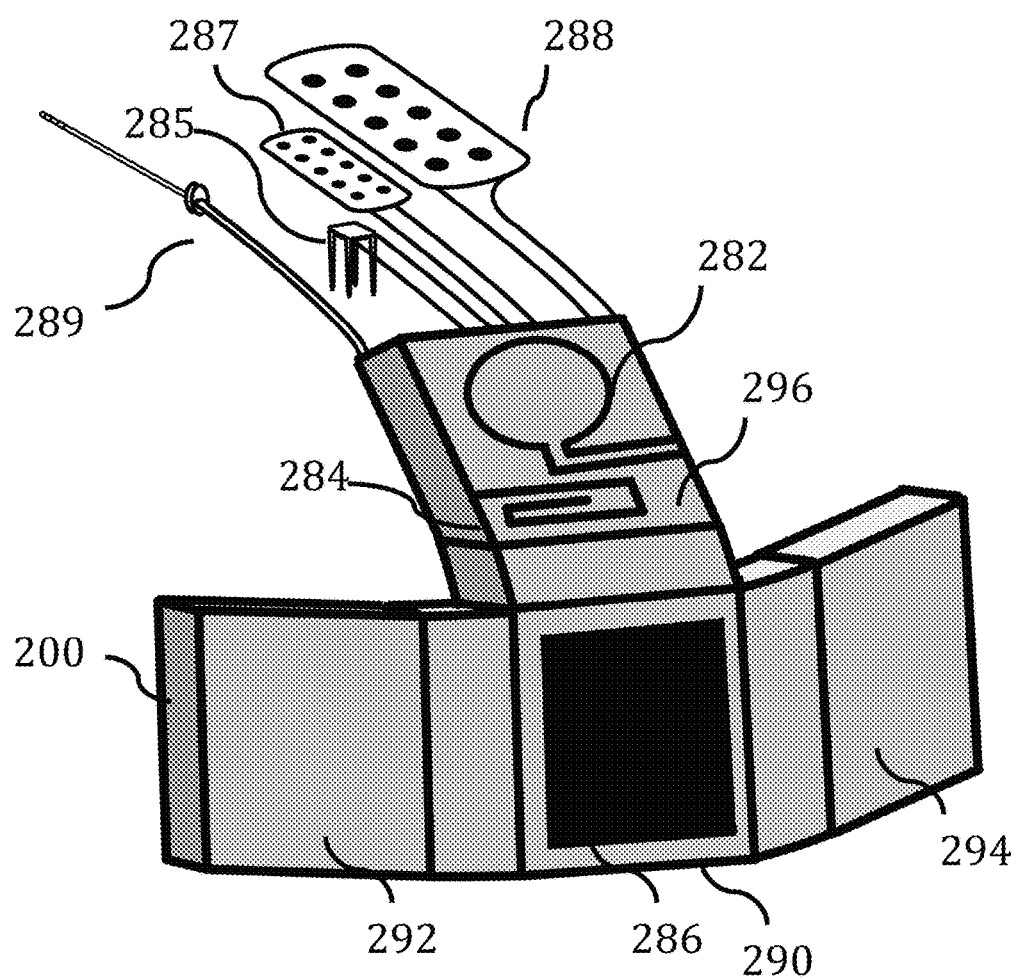
Figure 5B:
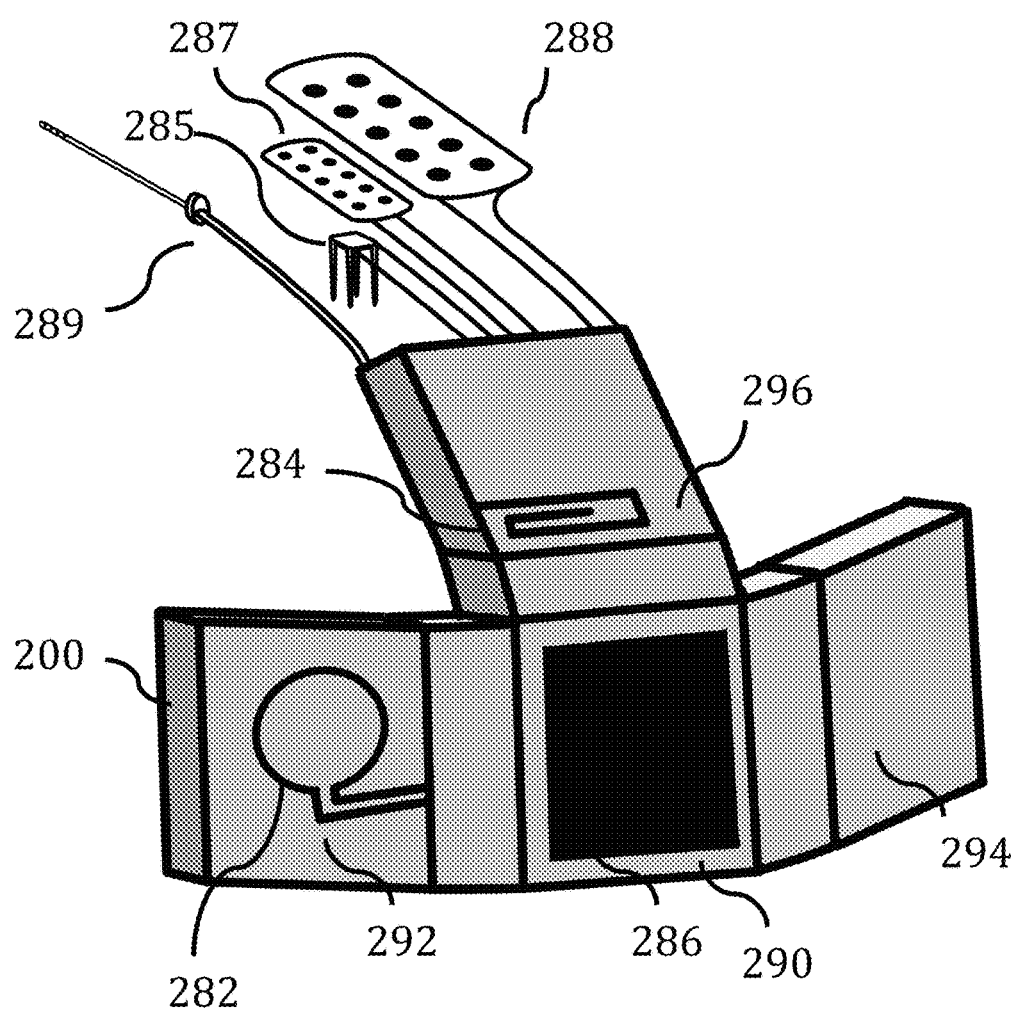

FIG. 5 shows an isometric view of a device 200 with an inductive power coil 282, a radio frequency antenna 284, and a battery 286. In some embodiments, the inductive power coil 282 and radio frequency antenna 284 are located in the zone 296 of device 200. In other embodiments, the battery 286 is located in zone 290 of device 200. In still other embodiments, any number of electronic components such as the inductive power coil 282, radio frequency antenna 284, and battery 286 can be located collectively or individually in zone 290, zone 292, zone 294, zone 296 or any zone within device 200, on the same panel, or on separate panels. Any electronic component can be located in any position within device 200. In some embodiments, the implantable neural electrode 288 can be located in zone 290, zone 292, zone 294, zone 296 or any zone within device 200. FIG. 5A illustrates an embodiment of a device 200 that can include any number of elements of FIG. 5. Also illustrated are microelectrode array 285, stimulation lead 287, electrocorticography (ECoG) sensor 288, and deep brain stimulation lead 289 operably connected to device 200, as non-limiting examples of other elements that can be connected to one, two, or more devices. FIG. 5B illustrates an embodiment of a device 200 similar to FIG. 5A with power coil 282 and antenna 284 on different zones or panels 292, 296. Any number of components, including the aforementioned ones, can be on the same or different panels/zones in some embodiments.

Figure 6:
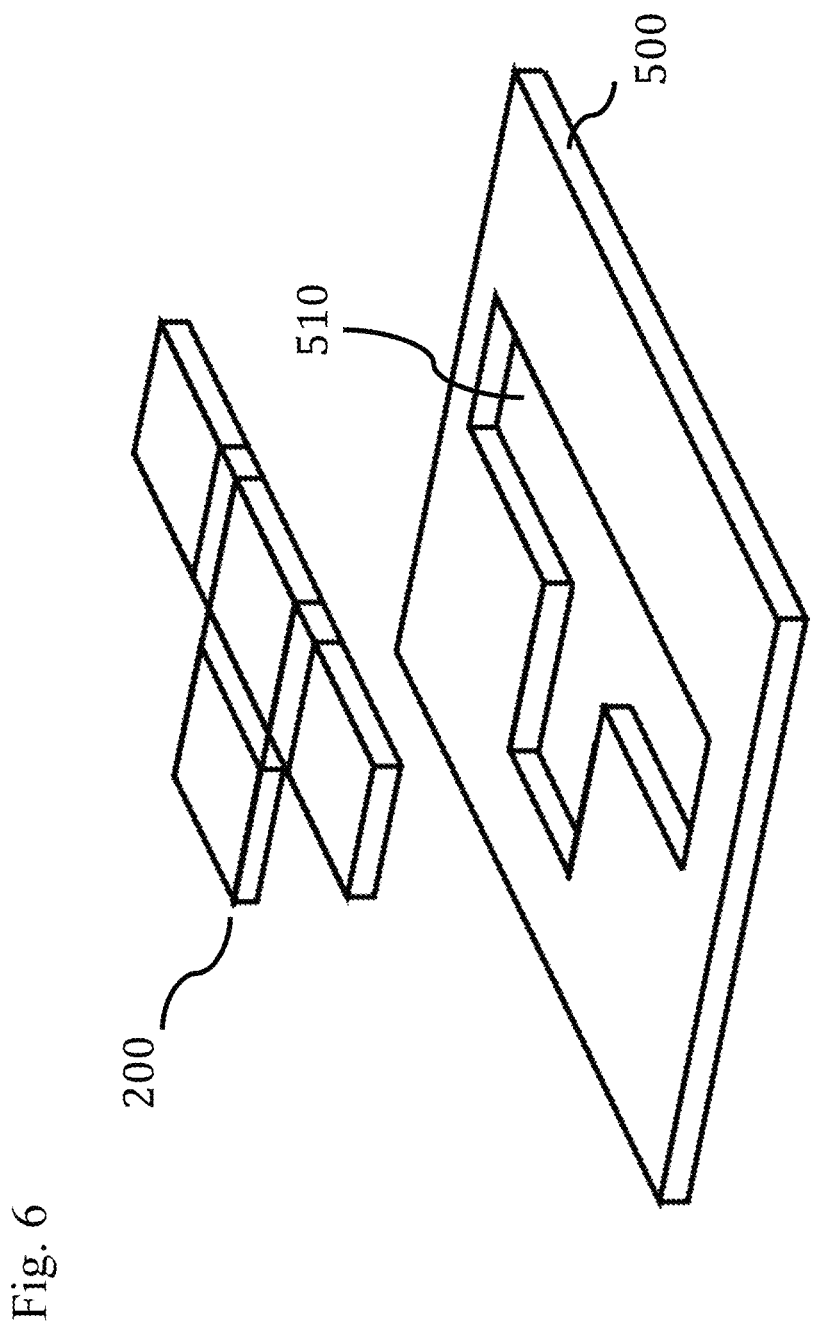
FIG. 6 shows an isometric view of a device above a holder for the device.

FIG. 6 shows an isometric view of a device 200 above a holder 500 with an opening 510 configured to be complementary or substantially complementary to the outer perimeter of the device as shown. In some embodiments, device 200 is placed in opening 510 to prevent deformation of device 200. In some embodiments, device 200 is placed in opening 510 to prevent creep or stress relaxation within device 200.

Figure 7:
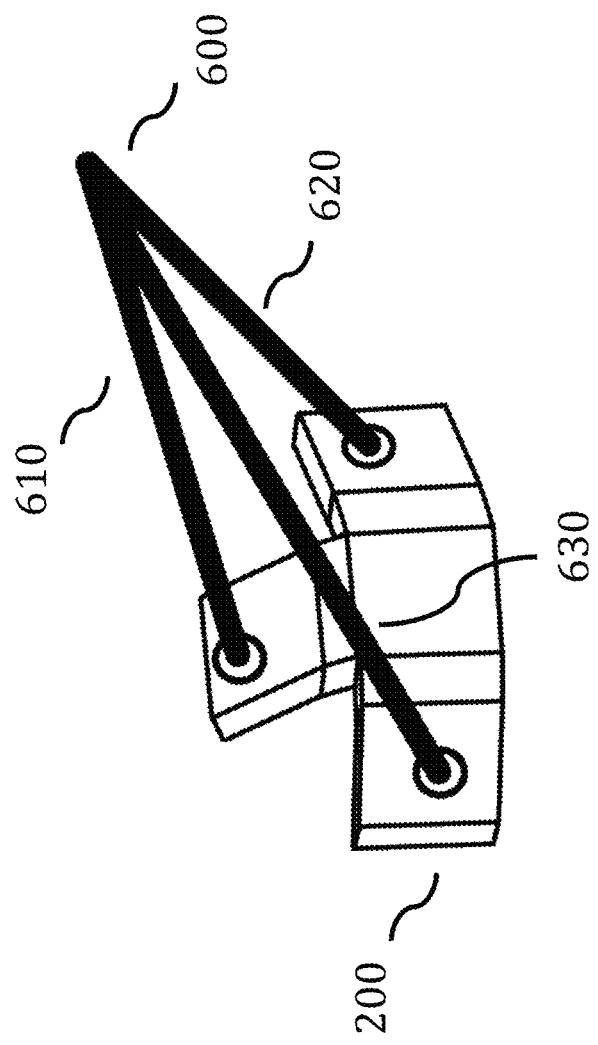
FIG. 7 shows an isometric view of a device engaged with the distal ends of an assistive assembly device.

FIG. 7 shows an isometric view of a device 200 engaged by an assembly device 600. In some embodiments, the assembly device 600 contains individual rods 610, 620, and 630 connected at one end to the assembly device 600. In some embodiments, a method for assembly and removal of device 200 from tissue involves an assembly device 600 that disengages and engages one or more zones of the device. In still other embodiments, the rods 610, 620, and 630 can contain magnetic material at their distal ends. In other embodiments, the magnetic material at the ends of rods 610, 620, and 630 can be magnetically attracted to engage with magnetic material zones in device 200. In other embodiments, the distal end or ends of device 600 could take the form of complementary reversible locking mechanisms such as, for example, a hook, a four bar linkage, a sliding component, grasping jaws, a multi-headed hook, a vacuum head, a bayonet lock mechanism, a hook and loop fastener, a snap fit mechanism, an actuated press fit, and an articulated snaking mechanism. In some embodiments, a method can include removing the second neural interface device from the subject by placing a removal tool comprising a plurality of magnetic zones in contact with (or proximate to but not necessarily in contact with) the magnetic zones of the plurality of rigid panels; and withdrawing the removal tool along with the second neural interface device. In some embodiments, such tools can be advantageous to remove devices from animals (e.g., laboratory animals) housed in enclosures without necessarily needing to establish contact with the devices.

Figure 8:
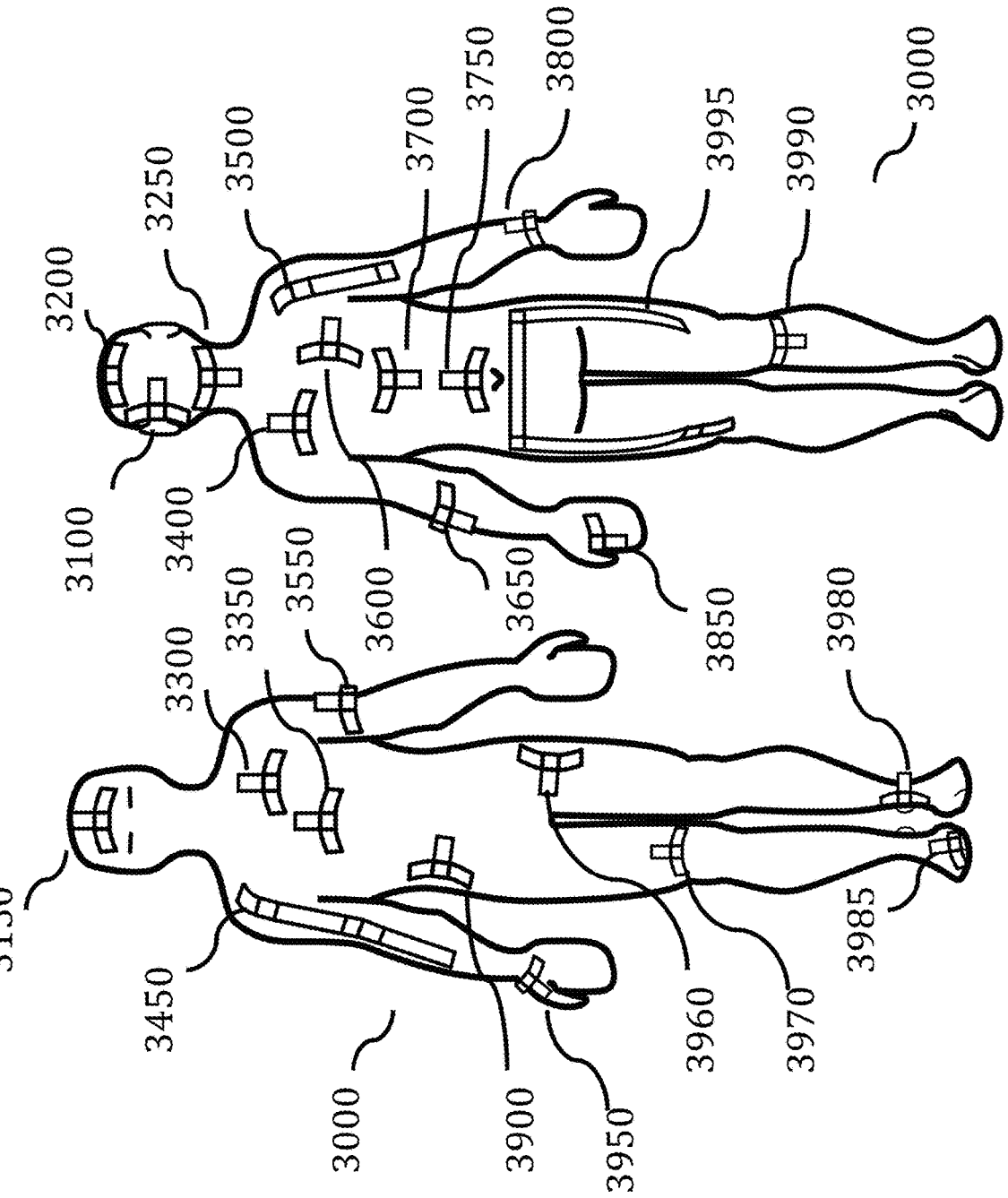
FIG. 8 shows a front and rear view of a body with devices assembled.

FIG. 8 shows a front and rear view of a body 3000 with devices 3100 with non-limiting examples of anatomical placement sites (near ears), 3150 (frontal scalp), 3200 (occipital scalp), 3250 (back of neck), 3300 (left chest), 3350 (mid-sternum), 3400 (left side of back), 3450 (front of shoulder/arm), 3500 (back of shoulder/arm), 3550 (upper arm), 3600 (upper mid-back), 3650 (back of elbow), 3700 (spine/mid back), 3750 (lower back), 3800 (wrist), 3850 (hands), 3900 (torso), 3950 (wrist), 3960 (hip), 3970 (knee), 3980 (ankle), 3985 (foot), 3990 (back of knee), and 3995 (thigh) movably positioned on it. In some embodiments, the device 3100 can conform around one or two ears. In some embodiments, panels of the devices are shaped to better conform to an anatomical target. The anatomical locations could be transcutaneous, percutaneous, and/or implanted in the body. In some embodiments, one or more of devices is placed on one or both lower extremities, upper extremities, the spine, the cranium, or combinations of the foregoing. In some embodiments, the devices are shaped to conform to non-human anatomy, including non-human primates (NHPs), pigs, cats, rabbit, sheep, cows, dogs, birds, and rodents.

In some embodiments, the implanted device is placed at a location beneath the skin, such as subcutaneously, or anywhere interior to the body. In other embodiments, the implant is placed beneath organs. In still other embodiments, the bone is shaped to provide additional clearance for placement of the implant and increase the strength of wireless communication. In other embodiments, the device is placed within tissue at some location below the skin, such as, for example, adjacent the Intrinsic cardiac ganglia, Cardiac plexus, Cardiac ganglion, Nodose ganglion, Structure of superior cervical ganglion, Sympathetic ganglion, Stellate ganglion, Postganglionic sympathetic nerve fibers of neck and thorax, Peripheral ganglia, Sensory ganglia, Spinal ganglia, Auricular branch of the vagus (ABVN), Nucleus tractus solitarius (NTS), Dorsal medullary vagal system, Spinal cord, Peripheral neurons innervating the bladder, Peripheral and spinal neural circuitry of the lower urinary tract (LUT), Sensory and autonomic neurons that innervate the bladder body, trigone and proximal urethra, Vagal branches innervating the stomach, Nerves projecting to the intrapulmonary airways, Preganglionic parasympathetic nerves innervating the airways, Superior cervical ganglia (SCG), Hypoglossal nerve, Structure of parasympathetic ganglion, Enteric nervous system (ENS), ganglia of the ENS intrinsic to the gut wall, the Vagus nerve (VN), or in between any of the foregoing structures. In some embodiments, the internal device can be placed on an endothelial, mesothelial, or adventitial layer of tissue, for example, or under or within the epidermis, dermis, or hypodermis of the skin. In some embodiments, the device is placed within the skeleton, organs, nails, hair, ear, finger, hand, nose, nostril, eye, tongue, tooth, or teeth. In some embodiments, the implanted device is placed proximate the ulnar, median, radial, sciatic, tibial, saphenous, and/or other nerves.

In some embodiments, the implanted device is placed at a location beneath the scalp. In other embodiments, the implant is placed beneath the cranium. In still other embodiments, the bone is shaped to provide additional clearance for placement of the implant and increase the strength of wireless communication. In other embodiments, the device is placed within tissue at some location below the skull/cranium, such as, for example, deep to the skull, dura mater, arachnoid, pia mater, or bridging veins, and/or superficial to, or in between any of the foregoing structures. In some embodiments, the internal device can be placed on an endothelial, mesothelial, or adventitial layer of tissue, for example, or under or within the epidermis, dermis, or hypodermis of the skin.

Figure 9:
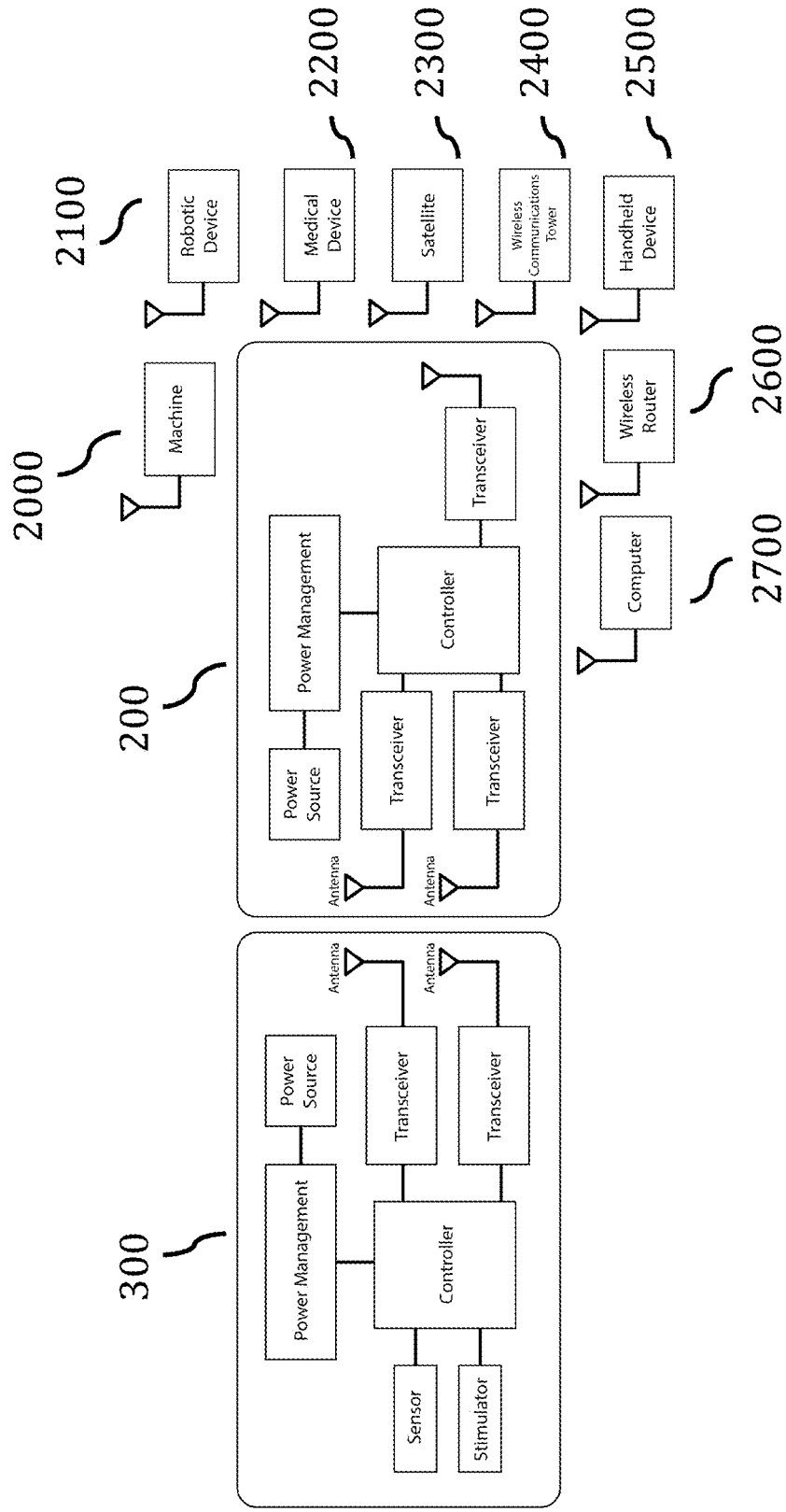
FIG. 9 illustrates a block diagram of a wireless system, according to some embodiments.

FIG. 9 illustrates a block diagram of a wireless system. In some embodiments, the device 200 can operably wirelessly communicate with an implanted device 300. In some embodiments, the device 200 can operably transmit power to an implanted device 300. In some embodiments, the device 200 can operably wirelessly communicate with devices including a computer 2700, a wireless router 2600, a hand held device 2500, a wireless communication tower 2400, a satellite 2300, a medical device 2200, a robotic device 2100, and a machine 2000.

Figure 10:
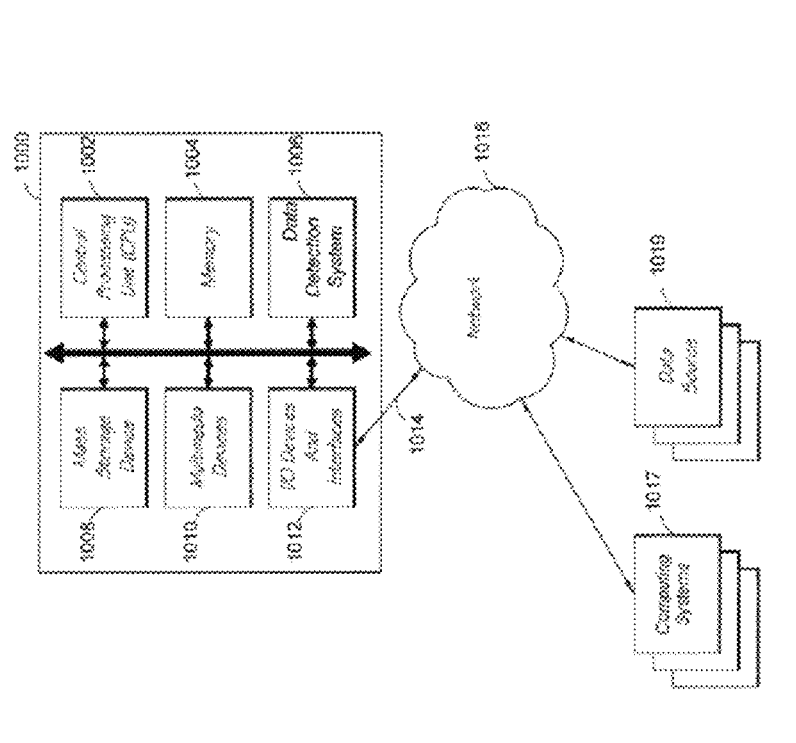
FIG. 10 illustrates a computer system that can be configured for use with a wireless neural data system, according to some embodiments.

FIG. 10 is a block diagram depicting an embodiment of a computer hardware system configured to run software for implementing one or more embodiments of the systems described herein.

In some embodiments, the computer devices, clients, and/or servers described herein take the form of a computing system 1000 illustrated in FIG. 10 which is a block diagram of one embodiment of a computing system that is in communication with one or more computing systems 1017 and/or one or more data sources 1019 via one or more networks 1016. The computing system 1000 may be used to implement one or more of the systems and methods described herein. In addition, in one embodiment, the computing system 1000 may be configured to manage access or administer a software application. While FIG. 10 illustrates one embodiment of a computing system 1000, it is recognized that the functionality provided for in the components and modules of computing system 1000 may be combined into fewer components and modules or further separated into additional components and modules.

In one embodiment, the computing system 1000 comprises an encoding and/or decoding module 1006 that carries out the functions described herein with reference to detecting and/or processing data, including any one of the techniques described above. The data detection system module 1006 and/or other modules or functional units disclosed herein may be executed on the computing system 1000 by a central processing unit 1002 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

Generally, the modules described herein refer to logical modules that may be combined with other modules or divided into sub-modules despite their physical organization or storage.

In one embodiment, the computing system 1000 also comprises a mainframe computer suitable for controlling and/or communicating with large databases, performing high volume transaction processing, and generating reports from large databases. The computing system 1000 also comprises a central processing unit ("CPU") 1002, which may comprise a conventional microprocessor. The computing system 1000 further comprises a memory 1004, such as random access memory ("RAM") for temporary storage of information and/or a read only memory ("ROM") for permanent storage of information, and a mass storage device 1008, such as a hard drive, diskette, or optical media storage device. Typically, the modules of the computing system 1000 are connected to the computer using a standards based bus system. In different embodiments, the standards based bus system could be Peripheral Component Interconnect (PCI), Microchannel, SCSI, Industrial Standard Architecture (ISA), and Extended ISA (EISA) architectures, for example.

The computing system 1000 comprises one or more commonly available input/output (I/O) devices and interfaces 1012, such as a keyboard, mouse, touchpad, and printer. In one embodiment, the I/O devices and interfaces 1012 comprise one or more display devices, such as a monitor, that allows the visual presentation of data to a user.

More particularly, a display device provides for the presentation of GUIs, application software data, and multimedia presentations, for example. In one or more embodiments, the I/O devices and interfaces 1012 comprise a microphone and/or motion sensor that allow a user to generate input to the computing system 1000 using sounds, voice, motion, gestures, or the like. In the embodiment of FIG. 10, the I/O devices and interfaces 1012 also provide a communications interface to various external devices. The computing system 1000 may also comprise one or more multimedia devices 1010, such as speakers, video cards, graphics accelerators, and microphones, for example.

The computing system 1000 may run on a variety of computing devices, such as, for example, a server, a Windows server, a Structure Query Language server, a Unix server, a personal computer, a mainframe computer, a laptop computer, a tablet computer, a cell phone, a smartphone, a personal digital assistant, a kiosk, an audio player, an e-reader device, and so forth. The computing system 1000 is generally controlled and coordinated by operating system software, such as z/OS, Windows 95, Windows 98, Windows NT, Windows 2000, Windows XP, Windows Vista, Windows 10, Windows 8, Linux, BSD, SunOS, Solaris, Android, iOS, BlackBerry OS, or other compatible operating systems. In Macintosh systems, the operating system may be any available operating system, such as MAC OS X. In other embodiments, the computing system 1000 may be controlled by a proprietary operating system. Conventional operating systems control and schedule computer processes for execution, perform memory management, provide file system, networking, and I/O services, and provide a user interface, such as a graphical user interface ("GUI"), among other things.

In the embodiment of FIG. 10, the computing system 1000 is coupled to a network 1016, such as a LAN, WAN, or the Internet, for example, via a wired, wireless, or combination of wired and wireless, communication link 1014. The network 1016 communicates with various computing devices and/or other electronic devices via wired or wireless communication links. In the embodiment of FIG. 3, the network 1016 is communicating with one or more computing systems 1017 and/or one or more data sources 1019.

Access to the data detection system module 1006 of the computer system 1000 by computing systems 1017 and/or by data sources 1019 may be through a web-enabled user access point such as the computing systems' 1017 or data source's 1019 personal computer, cellular phone, smartphone, laptop, tablet computer, e-reader device, audio player, or other device capable of connecting to the network 1016. Such a device may have a browser module that is implemented as a module that uses text, graphics, audio, video, and other media to present data and to allow interaction with data via the network 1016.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 1012 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1000 may comprise a physical or logical connection established between a remote microprocessor and a mainframe host computer for the express purpose of uploading, downloading, or viewing interactive data and databases on-line in real time. The remote microprocessor may be operated by an entity operating the computer system 1000, including the client server systems or the main server system, an/or may be operated by one or more of the data sources 1019 and/or one or more of the computing systems 1017. In some embodiments, terminal emulation software may be used on the microprocessor for participating in the micro-mainframe link.

In some embodiments, computing systems 1017 who are internal to an entity operating the computer system 1000 may access the data detection system module 1006 internally as an application or process run by the CPU 1002.

In an embodiment, a user access point or user interface comprises a personal computer, a laptop computer, a tablet computer, an e-reader device, a cellular phone, a smart-phone, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, a smartphone, a smartwatch, or the like.

In addition to the systems that are illustrated in FIG. 10, the network 1016 may communicate with other data sources or other computing devices. The computing system 1000 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

FIGS. 11-11B illustrate embodiments of an implantable device configured to be aligned with a second device (not shown) that can be an external device in some cases. FIG. 11 shows two parts of an embodiment of a device, section 100 and section 112 adjacent tissue 60. Sections 100 and 112 can include rigid panels, and one or both could include a magnet, and can have many shapes including a ring, square, oval, ellipse, rectangle and others. Section 112 can include ridges on it to prevent rotation against tissue. The magnet, illustrated here in the shape of a ring 112, can be fastened to tissue 60 (e.g., bone or other tissue) by a screw or suture 298 through the center of the ring 112. In some embodiments, the magnet is encapsulated in a hermetic assembly for human use.

FIG. 11A shows two parts of a device, section 100 and section 112 adjacent tissue 60. Section 112 is held against the tissue by a screw 298 or other fixation mechanism. Section 112 can be held against tissue by a suture, adhesive, and other means.

Figure 11C:
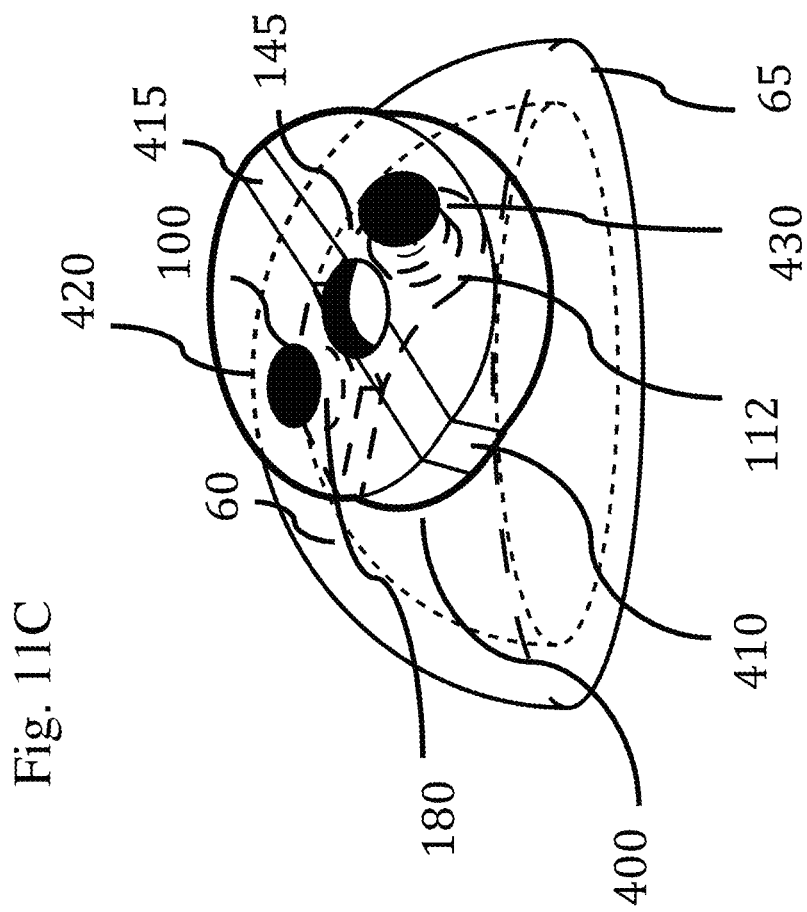
FIG. 11C illustrates an implanted device aligned with an external device via magnets.

FIG. 11B shows three parts of a device, section 100, section 112, and section 145 adjacent tissue 60. Section 145 can be a flexible section, such as a backing layer to connect sections 100 and 112, and have increased flexibility with respect to sections 100 and 112. Section 145 can also be a flexible and non-stretchable section, and be removable or non-removable with respect to sections 100 and 112. Section 145 can position section 112 relative to section 100 so that other devices will align with sections 100 and 112 accurately. Section 145 can be covered by tissue, or removed from sections 100 and 112 after sections 100 and 112 are positioned. In some embodiments, section 100 can be free-floating and not attached to section 112, and include an internal power source, but no magnets. As such, improved conformance can occur without necessarily requiring any movable structures. In some embodiments, section 100 includes eyelets configured to house a screw or other fixation device therethrough such that section 100 is also directly fixed to a substrate along with section 112. In some embodiments, section 100 can include a magnetic element with a first magnetic force strength, and section 112 includes a magnetic element with a second magnetic force strength that is about or at least about 10%, 20%, 30%, 40%, 50%, 75%, 100%, or more stronger than the first magnetic force strength. In other words, part 100 might have a "light" magnetic force zone to orient a high data rate communication element (which doesn't need as tight an alignment as the power coil). The "anchor" ring magnet on 112 could hold in place the heaviest portion of a worn device alignable with the implanted device, and the worn device could also have a lightweight section connected by a movable structure that is aligned magnetically to wirelessly communicate with the section 100. In some embodiments, the magnet of section 112 could in some cases take up about or more than about 25%, 50%, 75%, or more of the surface area of section 112, while the magnet of section 100 could in some cases take up about or less than about 75%, 50%, 25%, or less of the surface area of section 100. FIG. 11C illustrates an embodiment of a system illustrating an implanted device as described with respect to FIGS. 11-11B above, with an external device 400 including movable structure zones 410, 415, and magnets 420, 430 configured to align with magnets of sections 100, 112 of the implanted device. As illustrated the external device 400 (shown here with an arcuate geometry) need not necessarily have the same geometry as the implanted device, so long as the magnets of both devices are alignable.

In some embodiments, a system can include a neural interface device operably connected to a flexible backing layer with a spaced-apart magnetic element that can be configured to fixed with a screw, suture, or other fixation mechanism to tissue. The flexible backing layer can be sized such that the device is connected to a first end of the flexible backing layer, and the magnetic element can be connected to a second end of the flexible backing layer. In some cases the flexible backing layer can advantageously allow for accurate positioning (e.g., the spaced apart distance) of the magnetic element with respect to the neural interface device. The flexible backing layer can remain in the body, or removed after implantation of the neural interface device and the magnetic element. The flexible backing layer can be non-stretchable in some cases. The flexible backing layer can be biodegradable or nonbiodegradable in some cases, and be removable by cutting, a frangible or perforated tear-away zone, or other features. The flexible backing layer could have the same or substantially the same wall thickness as the device and/or magnetic element to reduce tissue irritation and/or response. In some embodiments, the magnetic element can be encased in a housing, such as a metal housing (e.g., titanium) or a polymer for example.

Other devices can also have adjustable sections to compensate for inaccuracies in positioning section 100 and section 112. Removing section 145 reduces the amount of material implanted within tissue and reduces the response of the body. Section 145 can also have the same thicknesses as section 100 and section 112 to minimize tissue response.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A neural interface system, comprising:
a first neural interface device and a second neural interface device, each of the first neural interface device and second neural interface device comprising at least two rigid panels, each rigid panel operably connected to an adjacent rigid panel by at least one movable structure in between adjacent rigid panels and configured to substantially conform to tissue in a first configuration and a second configuration different from the first configuration, wherein each rigid panel of both the first neural interface device and the second neural interface device comprises magnetic zones and non-magnetic zones,
wherein the first neural interface device is configured to be wearable above a skin surface of a subject;
wherein the second neural interface device is configured to be implantable below the skin surface of the subject;
wherein the first neural interface device and the second neural interface device are configured to movably align with each other via the magnetic zones; and
wherein the at least one movable structure comprises a hinge.

2. The neural interface system of claim 1, wherein the first neural interface device and the second neural interface device each comprise at least two magnetic zones configured to align the first neural interface device and the second neural interface device over a range of substrate contour geometries.

3. The neural interface system of claim 1, wherein the first neural interface device and the second neural interface device are configured to be in wireless communication with each other.

4. The neural interface system of claim 3, wherein the first neural interface device and the second neural interface device are configured to be in ultra wide band (UWB) wireless communication with each other.

5. The neural interface system of claim 3, wherein the first neural interface device and the second neural interface device comprise inductive coils configured for wireless power transmission.

6. The neural interface system of claim 1, wherein the second neural interface device comprises at least one sensor configured to wirelessly send data.

7. The neural interface system of claim 1, wherein the first neural interface device comprises a controller configured to wirelessly receive data from the at least one sensor.

8. The neural interface system of claim 7, wherein the second neural interface device comprises at least one neural effector, and the controller of the first neural interface device is further configured to wirelessly send instructions to adjust parameters of the at least one neural effector based on the data from the at least one sensor.

9. A method of positioning a neural interface system, comprising:
implanting a first neural interface device under a skin surface of a subject, wherein the first neural interface device comprises a plurality of rigid panels connected by at least one movable structure, each rigid panel of the first neural interface device comprising a magnetic zone and a non-magnetic zone;
positioning a second neural interface device on or above the skin surface of the subject, wherein the second neural interface device comprises a plurality of rigid panels connected by at least one movable structure, each rigid panel of the second neural interface device comprising a magnetic zone and a non-magnetic zone;
aligning the first neural interface device with the second neural interface device, wherein aligning occurs via magnetic attraction of the magnetic zones of the first neural interface device and the second neural interface device; and
removing the second neural interface device from the subject by placing a removal tool comprising a plurality of magnetic zones in contact with or not in contact with, but in magnetic proximity to the magnetic zones of the plurality of rigid panels and withdrawing the removal tool along with the second neural interface device.

10. The method of claim 9, wherein the first neural interface device and the second neural interface device substantially conform with tissue after aligning, and as the tissue moves.

11. The method of claim 9, wherein the second neural interface device is positioned on a location spaced apart above the skin surface of the subject.

12. The method of claim 9, wherein the second neural interface device is positioned directly on the skin surface of the subject.

13. A neural interface system, comprising:
a first neural interface device and a second neural interface device, each of the first neural interface device and second neural interface device comprising at least two rigid panels, each rigid panel configured to substantially conform to tissue in a first configuration and a second configuration different from the first configuration, wherein each rigid panel of both the first neural interface device and the second neural interface device comprises magnetic zones and non-magnetic zones,
wherein the first neural interface device is configured to be wearable above a skin surface of a subject;
wherein the second neural interface device is configured to be implantable below the skin surface of the subject;
wherein the first neural interface device and the second neural interface device are configured to movably align with each other via the magnetic zones; and
wherein the first neural interface device comprises a hinge.

14. The neural interface system of claim 13, wherein the first neural interface device and the second neural interface device comprise magnetic zones configured to align the first neural interface device and the second neural interface device.

15. The neural interface system of claim 13, wherein the first neural interface device and the second neural interface device are configured to be in wireless communication.

16. The neural interface system of claim 13, wherein the first neural interface device and the second neural interface device are configured to be in ultra wide band (UWB) wireless communication.

17. The neural interface system of claim 13, wherein the first neural interface device and the second neural interface device comprise inductive coils.

18. The neural interface system of claim 13, wherein the second neural interface device comprises at least one sensor.

19. The neural interface system of claim 18, wherein the first neural interface device comprises a controller configured to receive data from the at least one sensor.

20. The neural interface system of claim 19, wherein the second neural interface device comprises at least one neural effector, and the controller of the first neural interface device is further configured to send instructions to the at least one neural effector.

* * * * *

UNITED STATES PATENT AND TRADEMARK OFFICE
CERTIFICATE OF CORRECTION

PATENT NO. : 11,065,439 B1
APPLICATION NO. : 16/216797
DATED : July 20, 2021
INVENTOR(S) : Ian Loren Halpern Page 1 of 1

It is certified that error appears in the above-identified patent and that said Letters Patent is hereby corrected as shown below:

In the Specification

In Column 14, Line 31, delete "0.10" and insert --0.1°--.

In Column 14, Line 32, delete "7°"" and insert --7°,--.

In Column 14, Line 32, delete "102," and insert --10°,--.

In the Claims

In Column 25, Line 67, Claim 7, delete "the at" and insert --at--.

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*